United States Patent
Swissler et al.

(10) Patent No.: US 11,305,421 B2
(45) Date of Patent: Apr. 19, 2022

(54) METHOD AND SYSTEM FOR JOINING ROBOTIC COMPONENTS

(71) Applicant: Northwestern University, Evanston, IL (US)

(72) Inventors: Petras J. Swissler, Evanston, IL (US); Michael S. Rubenstein, Wilmette, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/973,373

(22) PCT Filed: Jun. 11, 2019

(86) PCT No.: PCT/US2019/036458
§ 371 (c)(1),
(2) Date: Dec. 8, 2020

(87) PCT Pub. No.: WO2019/241185
PCT Pub. Date: Dec. 19, 2019

(65) Prior Publication Data
US 2021/0252696 A1      Aug. 19, 2021

Related U.S. Application Data

(60) Provisional application No. 62/683,351, filed on Jun. 11, 2018.

(51) Int. Cl.
*B25J 9/08*    (2006.01)
*B25J 11/00*   (2006.01)
(Continued)

(52) U.S. Cl.
CPC .............. *B25J 9/08* (2013.01); *B25J 11/005* (2013.01); *B29C 65/4855* (2013.01);
(Continued)

(58) Field of Classification Search
CPC ........................................................ B25J 9/08
See application file for complete search history.

(56) References Cited

U.S. PATENT DOCUMENTS 5,100,494 A * 3/1992 Schmidt ................ B29C 65/342
                                                      156/712
5,286,327 A    2/1994 Swartz
(Continued)

OTHER PUBLICATIONS

Neubert et al., Soldercubes: a self-soldering self-reconfiguring modular robot system, Auton Robot, Jun. 2015, pp. 139-158 (Year: 2015).*

(Continued)

*Primary Examiner* — Scott W Dodds
(74) *Attorney, Agent, or Firm* — Bell & Manning, LLC

(57) ABSTRACT

A robot includes a power bus assembly configured to receive a voltage and a continuous dock. The robot also includes a microcontroller in communication with the power bus assembly and the continuous dock. The microcontroller is configured to determine that the continuous dock is in contact with a surface that results in a voltage differential between the continuous dock and the surface. The microcontroller is also configured to activate a motor to apply a force that presses the continuous dock against the surface. The voltage causes a current to flow from the continuous dock to the surface such that a portion of the continuous dock melts and forms a bond to the surface.

16 Claims, 18 Drawing Sheets

(51) Int. Cl.
    B29C 65/48      (2006.01)
    B29C 65/76      (2006.01)
    B29C 65/00      (2006.01)
    A61B 34/30      (2016.01)
    B29L 31/34      (2006.01)
    B29C 65/34      (2006.01)

(52) U.S. Cl.
    CPC ............ *B29C 65/76* (2013.01); *B29C 66/474*
            (2013.01); *B29C 66/72321* (2013.01); *B29C*
            *66/7392* (2013.01); *B29C 66/73141* (2013.01);
                *A61B 34/30* (2016.02); *B29C 65/3468*
                (2013.01); *B29L 2031/34* (2013.01)

(56)                References Cited

U.S. PATENT DOCUMENTS 5,523,662 A      6/1996  Goldenberg et al.
    6,243,622 B1     6/2001  Yim et al.
    2006/0234028 A1 10/2006  Pardo

OTHER PUBLICATIONS

Wang et al., Physical Connection and Disconnection Control Based on Hot Melt Adhesives, IEEE/ASME Transactions on Mechatronics, Jun. 2012, pp. 1397-1409 (Year: 2012).*
Swissler et al., FireAnt: A Modular Robot with Full-Body Continuous Docks. 2018 IEEE International Conference on Robotics and Automation (ICRA). May 2018. [retrieved on Sep. 18, 2019]. Retrieved from the Internet: URL: http://users.eecs.northwestern.edu/-mrubenst/ICRA_fireant.pdf.. entire document.
The International Search Report and Written Opinion dated Oct. 31, 2019 for International application No. PCT/US2019/036458; pp. 1-10.
Chris R. Reid et al., "Army ants dynamically adjust living bridges in response to a cost-benefit trade-off," PNAS, Dec. 8, 2015, vol. 112, No. 49; pp. 15113-15118.
Nathan J. Mlot et al., "Fire ants self-assemble into waterproof rafts to survive floods," PNAS, May 10, 2011, vol. 108, No. 19; pp. 7669-7673.
T.C. Schneirla et al., "The Army Ant: This explanation of how the creature conducts its complicated social life clearly distinguishes ants from men," 1948 Scientific American, Inc., pp. 16-23.
Barry M. Bumbiner, "Cell Adhesion: The Molecular Basis of Tissue Architecture and Morphogenesis," Cell, Feb. 9, 1996, vol. 84; pp. 345-357.
Mark Yim et al., "Modular Self-Reconfigurable Robot Systems [Grand Challenges of Robotics]," IEEE Robotics & Automation Magazine, Apr. 2007; pp. 1-11.
Justin Werfel et al., "Designing Collective Behavior in a Termite-Inspired Robot Construction Team," Science, Feb. 14, 2014, vol. 343; pp. 754-758.
Jose Baca et al., "ModRED: Hardware design and reconfiguration planning for a high dexterity modular self-reconfigurable robot for extra-terrestrial exploration," Robotics and Autonomous Systems (2014), vol. 62, pp. 1002-1015.
Michael Rubenstein et al., "Docking among independent and autonomous CONRO self-reconfigurable Robots," IEEE International Conference on Robotics and Automation, Jan. 2004; pp.
Kyle Gilpin et al., "Robot Pebbles: One Centimeter Modules for Programmable Matter Through Self-disassembly," IEEE, 2010; pp. 2485-2492.
John W. Romanishin et al., "M-Blocks: Momentum-driven, Magnetic Modular Robots," 2013 IEEE/RSJ International Conference on Intelligent Robots and Systems (IROS), Nov. 3-7, 2013. Tokyo, Japan; pp. 4288-4295.
Francesco Mondada et al., "Swarm-Bot: A New Distributed Robotic Concept," Autonomous Robots 2004, vol. 17; pp. 193-221.
Masahiro Shimizu et al., "An Amoeboid Modular Robot That Exhibits Real-time Adaptive Reconfiguration," The 2009 IEEE/RSJ International Conference on Intelligent Robots and Systems, Oct. 11-15, 2009 St. Louis, USA; pp. 1496-1501.
Melinda Malley et al., "Flippy: A Soft, Autonomous Climber with Simple Sensing and Control," 2017 IEEE/RSJ International Conference on Intelligent Robots and Systems (IROS) Sep. 24-28, 2017, Vancouver, BC, Canada; pp. 6533-6540.
Jonas Neubert et al., "A Robotic Module for Stochastic Fluidic Assembly of 3D Self-Reconfiguring Structures," 2010 IEEE International Conference on Robotics and Automation Anchorage Convention District May 3-8, 2010, Anchorage, Alaska, USA; pp. 2479-2484.
Proto-Pasta, "Proto-Pasta Conductive PLA Product Page," [Online]. Available: https://www.proto-pasta.com/products/conductivepla?variant=1265211484. [Accessed Aug. 30, 2017].

* cited by examiner

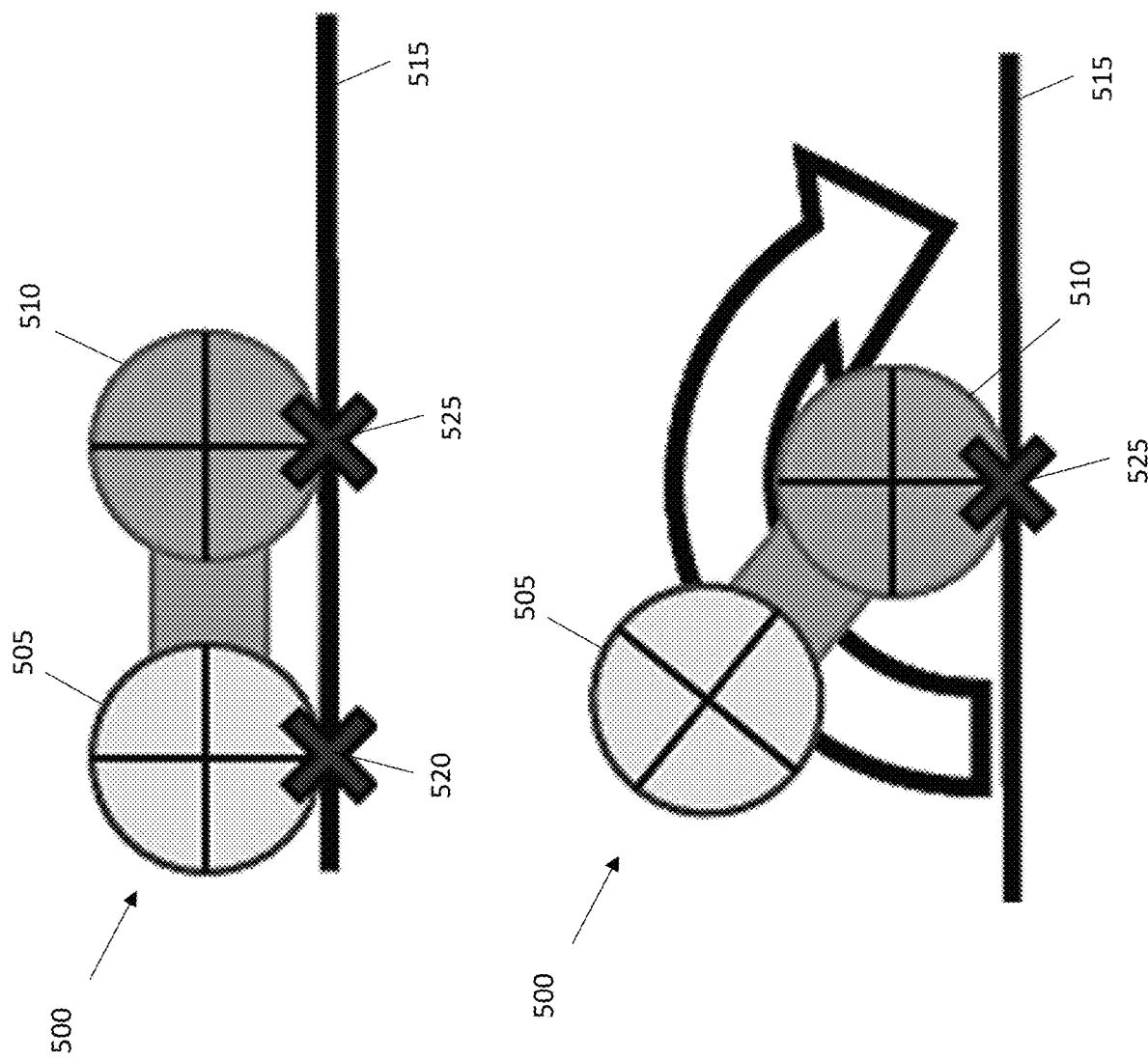

METHOD AND SYSTEM FOR JOINING ROBOTIC COMPONENTS

CROSS-REFERENCE TO RELATED APPLICATION

This application is a National Stage of International Application No. PCT/US19/36458, filed Jun. 11, 2019, which claims the benefit of U.S. Patent Application No. 62/683,351, filed Jun. 11, 2018, the contents of which are herein incorporated by reference.

BACKGROUND

Robotics is a scientific field that involves the design, fabrication, operation, and use of robots to achieve tasks. Robotics also involves the design and generation of computing systems to control the robots and perform information processing of data sensed or otherwise gathered by the robots. A robot can refer to any machine that is capable of automatically performing a series of actions to perform a task. In some fields, robots can be used to perform tasks that would otherwise be performed by a human, which can result in cost savings and increased efficiency. Additionally, robots can be used to perform tasks that are often dangerous for humans to perform (e.g., bomb deactivation), which can help to save lives.

SUMMARY

An illustrative robot includes a power bus assembly configured to receive a voltage and a continuous dock. The robot also includes a microcontroller in communication with the power bus assembly and the continuous dock. The microcontroller is configured to determine that the continuous dock is in contact with a surface that results in a voltage differential between the continuous dock and the surface. The microcontroller is also configured to activate a motor to apply a force that presses the continuous dock against the surface. The voltage causes a current to flow from the continuous dock to the surface such that a portion of the continuous dock melts and forms a bond to the surface.

An illustrative continuous dock includes a conductor in the form of a conductive mesh layer, a first conductive plastic layer positioned on a first side of the conductive mesh layer, and a second conductive plastic layer positioned on a second side of the conductive mesh layer such that the first conductive plastic layer and the second conductive plastic layer surround at least a portion of the conductive mesh layer. At least a portion of the first conductive plastic layer is melted to at least a portion of the second conductive plastic layer through openings in the conductive mesh layer. The continuous dock also includes a conductive wire attached to the conductive mesh layer, where the conductive wire extends through at least one of the first conductive plastic layer and the second conductive plastic layer. The conductive wire is configured to receive a voltage from a power source to melt at least one of the first conductive plastic layer and the second conductive plastic layer.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 5A depicts a robot with both of its continuous docks docked to a surface in accordance with an illustrative embodiment.

FIG. 5B depicts the robot with the first continuous dock detached from the surface such that the robot is able to flip over in accordance with an illustrative embodiment.

DETAILED DESCRIPTION

Figure 1:
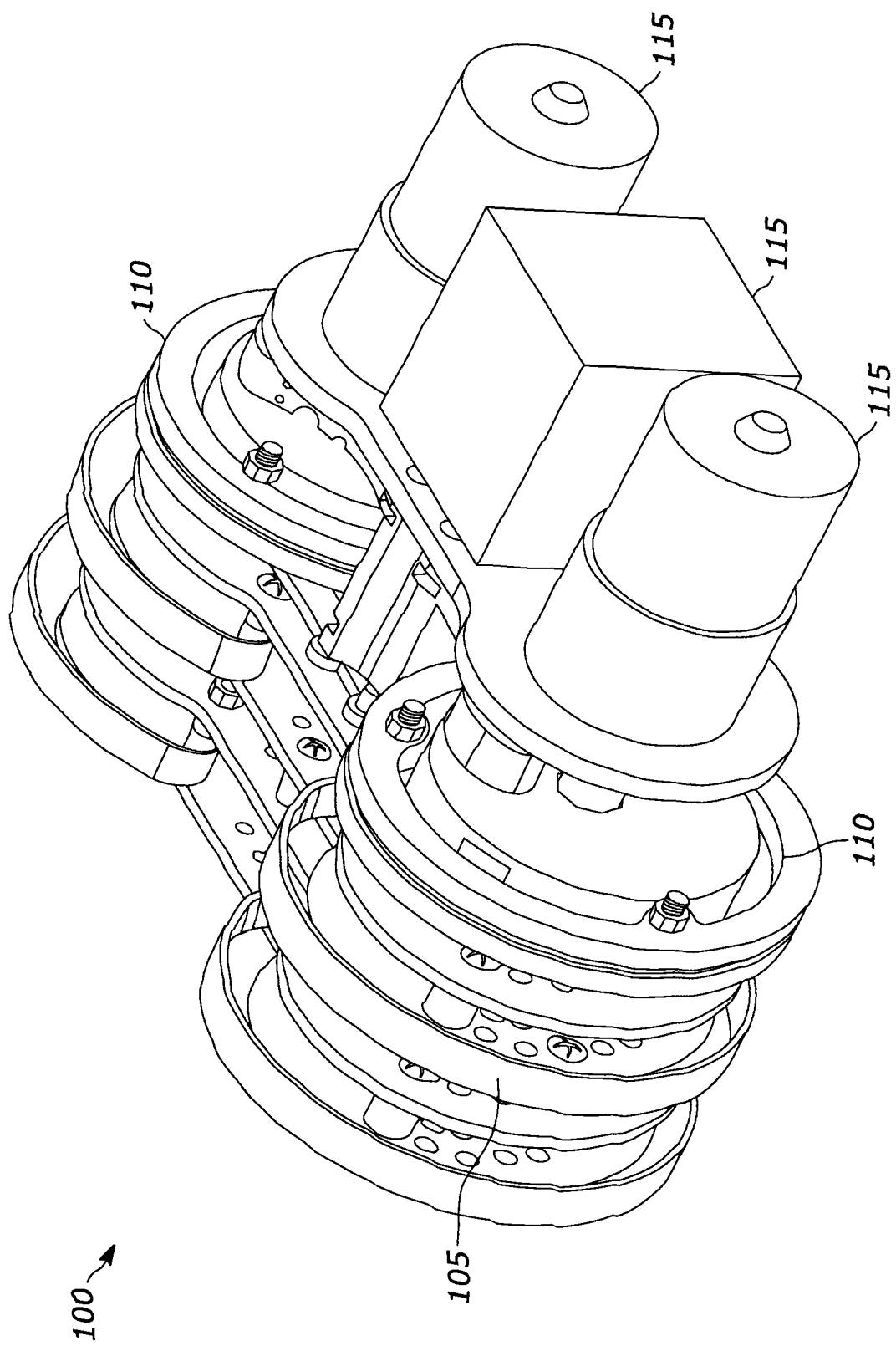
FIG. 1 is a perspective view of a robot in accordance with an illustrative embodiment.

It is well known in the natural world that insects are able to join together to form structures which can be used to accomplish tasks. For example, ants are able to join their bodies together to form bridges to cross gaps, rafts to protect against floods, and bivouacs to serve as temporary nests. Similarly, it can be desirable in certain applications to join multiple robotic components or units together to accomplish tasks. Traditional robotic systems that join robotic components together often require features to ensure alignment to specific locations on like robots, necessitating sensors to align mating points, or requiring magnets and other passive hardware to guide the attachment. Other robotic systems use grippers to attach to a full-body ring on another robot. This process involves alignment of the gripper, which limits the number and spontaneity of possible connections. These solutions increase dock complexity and often constrain the end-structure robot to a rigid lattice. Other robotic systems use genderless strips of material, such as Velcro®, to allow any individual robotic component to connect to any other individual robotic component regardless of relative orientation and without need for precise alignment. However, such systems are limited by the strength of the connection and cannot be used to build robust robotic structures.

Described herein are systems and methods for modular, self-assembling robots that eliminate the complexity imposed by precise alignment restrictions of traditional systems. The self-assembling robots are able to form strong, rigid, reversible connections while providing full body, dock anywhere flexibility. As discussed in detail herein, the self-assembling robots utilize continuous docks which melt to one another to form rigid connections. The continuous docks can be used to drive the robot's design, defining its footprint, dictating its locomotion, and allowing the robots to function with reduced sensor requirements as compared to traditional systems. The positioning of the continuous docks ensures that any approach by a compatible robot will result in contact between continuous docks, and the main modules of each robot can stack out-of-plane to maintain this footprint. In one embodiment, this design allows a robot to use these docks to traverse arbitrary arrangements of other robots by using a flipping motion as described below. In some embodiments, the robots operate on an included surface at an angle of 50° from horizontal, thus constraining the robot in-plane. In alternative embodiments, the robots can operate at other inclines.

More specifically, the continuous docks described herein allow two robots to join together in a strong, reversible attachment regardless of their relative orientations. The dock is mechanically straightforward and can include a conductive plastic bonded to a highly-conductive metal. In other embodiments, a layered mesh can be used as described in more detail below. When two such docks come into contact, a voltage can be applied across the connection, causing current to flow across the (arbitrary) point of contact, melting the plastic at this location and welding the two docks together. The dock detaches by re-applying the voltage to again heat the conductive plastic, which melts the plastic and releases the bond. This dock can be formed into arbitrary geometries and forms strong connections (e.g., a 1 kg robot using such docks can form a connection with a strength in excess of 20 kg). Additionally, pulsing low voltages across the connection allows robots to communicate with one another without melting the attachment material.

The robots described herein are mechanically and electronically straightforward and do not require the use of actuators. Attachments can be sensed using only a current sensor as opposed to limit switches and distance sensors as used in traditional systems. The robots are also able to attach to one another without the need for precise alignment, thereby reducing the need for robots to kinematically align prior to attachment and reducing mechanical and sensing requirements. The connections between robots are unilaterally reversible in that one robot can detach from another robot without prior interaction, Additionally, the formed attachments have a low detachment force which is approximately 0.5% of the break force. This is a significant improvement over an attachment mechanism such as Velcro® which has a detachment force equal to the break force.

A primary embodiment of the methods described herein is the formation of self-assembling structures such as robot-to-robot attachments, robot-to-surface attachments, and robot-to-object attachments. The methods and systems described herein can also be used as a general purpose Velcro® alternative to form strong attachments, as a semi-permanent alternative to traditional fasteners in the assembly of components that would otherwise be impossible or highly difficult to assemble, as a semi-permanent alternative to adhesives in the assembly of electronic devices (e.g., attachment of a screen to a phone), as a universal dock for reconfigurable lighting, microphone, or camera setup, as a readily reconfigurable and reusable brace for medical joint immobilization, as an alternative to a mechanical latch, etc.

FIG. 1 is a perspective view of a robot 100 in accordance with an illustrative embodiment. The robot 100 includes three primary modules in the form of a power bus unit 105, continuous docks 110, and an electronics and motors unit 115. In alternative embodiments, the robot 100 may include fewer, additional, and/or different modules. The power bus unit 105, which is described in more detail with reference to FIG. 3, is used to deliver power to the robot 100. The electronics and motors unit 115, described in more detail with reference to FIG. 4, includes one or motors to facilitate movement of the robot 100 and electronics to control the robot 100 such as a processor, memory, transceiver, interface, etc. The continuous docks 110, which are described in more detail with reference to FIG. 2, provide the interface through which robots are rigidly docked to one another. In an illustrative embodiment, the robot 100 includes an independent motor associated with each of the continuous docks 110 for a total of 2 motors. Alternatively, a single motor may be used to control a plurality of continuous docks. As depicted, the modules of the robot 100 are stacked out of plane such that any two robots which come into contact with one another will do so on their continuous docks. The power bus units of robots can also come into contact with one another such that a single powered robot can provide power to one or more other robots.

Figure 2A:
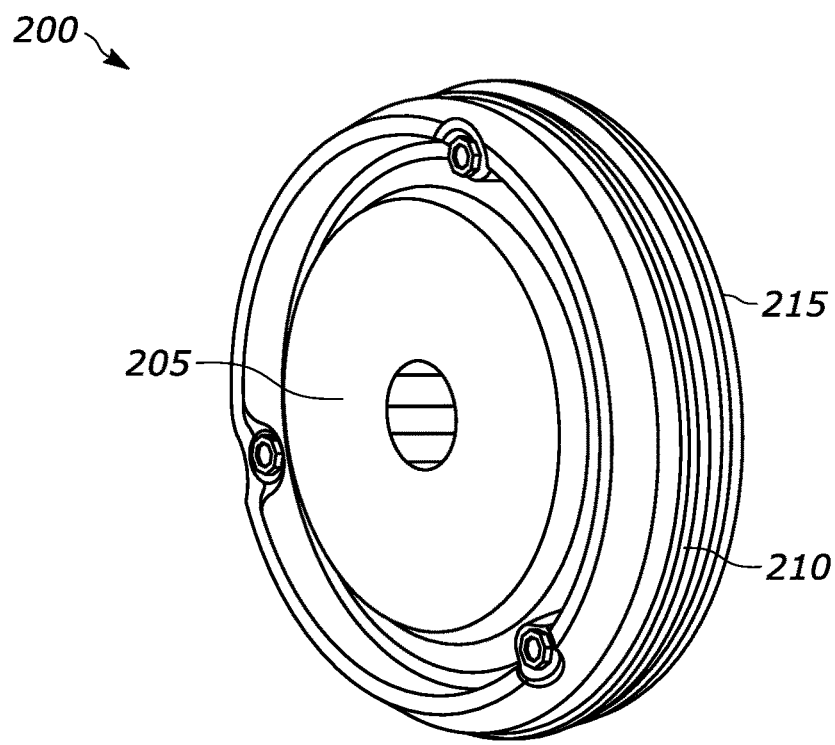
FIG. 2A depicts a continuous dock platform in accordance with an illustrative embodiment.
Figure 2B:
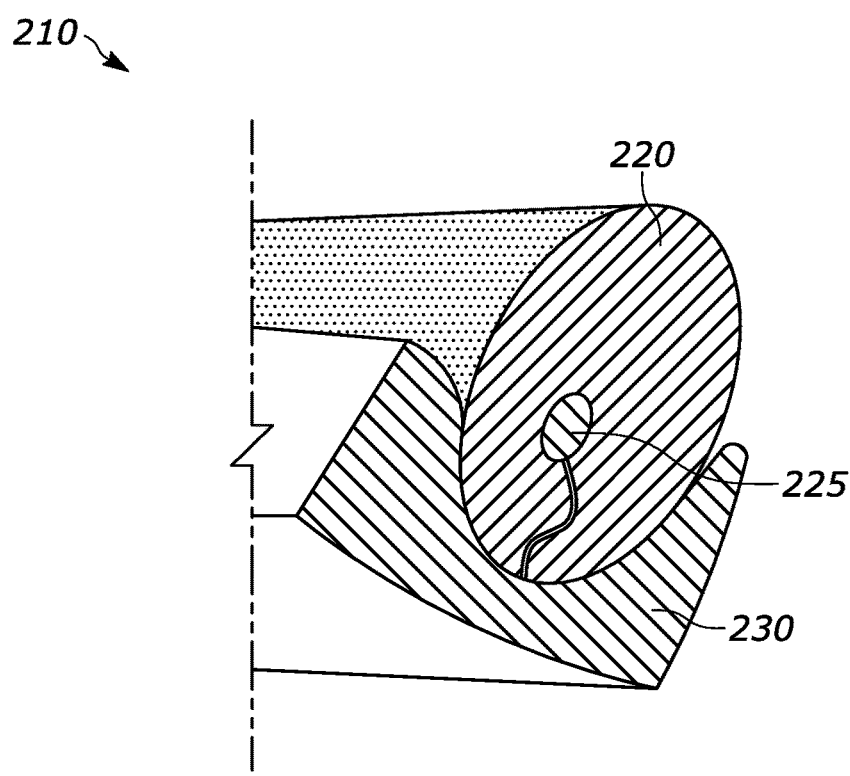
FIG. 2B is a partial cross-sectional view of a first continuous dock of the continuous dock platform shown in FIG. 2A in accordance with an illustrative embodiment.
Figure 3:
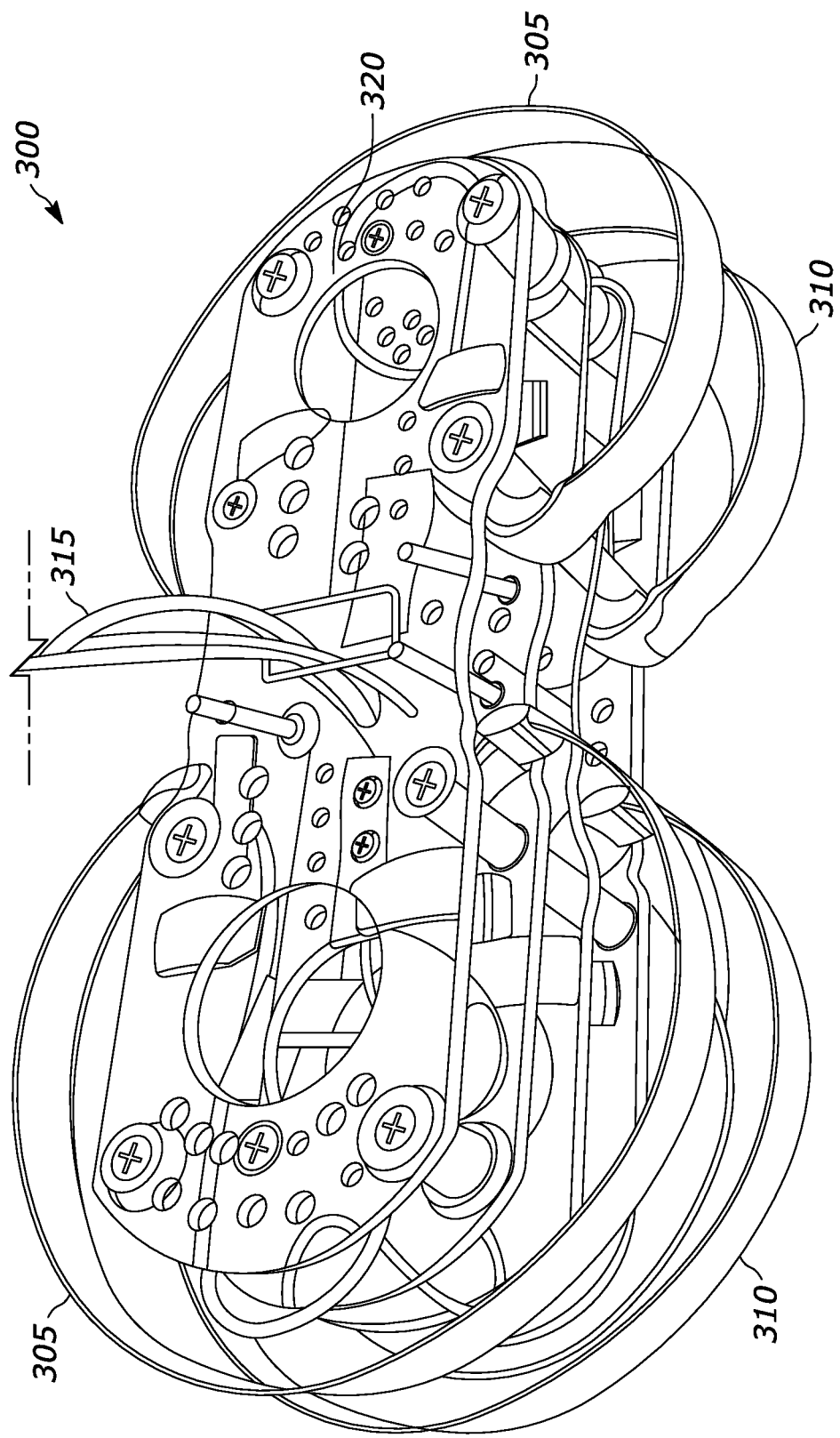
FIG. 3 depicts a power bus assembly for a robot n accordance with embodiment.

FIG. 2A depicts a continuous dock platform 200 in accordance with an illustrative embodiment. FIG. 2B is a partial cross-sectional view of a first continuous dock 210 of the continuous dock platform 200 in accordance with an illustrative embodiment. The continuous dock platform 200 includes a wheel 205, the first continuous dock 210, and a second continuous dock 215. In alternative embodiments, fewer or additional continuous docks may be used. Also, as discussed below, shapes other than a wheel may be used to form the continuous dock platform.

In an illustrative embodiment, the first continuous dock 210 and the second continuous dock 215 can be identical to one another. Alternatively, different shapes/form of continuous docks may be used on the same platform. The wheel 205 is formed from a conductive material, such as copper, such that a voltage applied to the wheel 205 will cause a current to flow across the wheel 205. In one embodiment, brushes attached to the main body of the robot make contact with the wheel 205, allowing the robot to apply a voltage to the continuous docks via the brushes. In another illustrative embodiment, each robot can include two continuous dock platforms. Alternatively, a robot may include fewer or additional continuous dock platforms. Additionally, although the continuous dock platform is depicted as a wheel in FIG. 2, it should be understood that the continuous dock platform can have a different three-dimensional shape such as square, triangle, rectangle, semi-sphere, sphere, etc.

As shown in FIG. 2B, the first continuous dock 210 includes a strip 220 of conductive plastic (i.e., a moderately-conductive meltable material) that includes a conductive wire 225 (i.e., a highly conductive material) that is embedded within the strip 220. The conductive wire 225 is attached to the wheel 205 such that a current applied to the wheel flows through the conductive wire 225. The first continuous dock 210 also includes a structural hoop 230 to increase dock rigidity. The strip 220 can be glued to the structural hoop 230, or attached using any other method known in the art. Gluing the strip 220 to the structural hoop 230 forms a strong and rigid continuous dock (or rim) with a resistance of between 100-300 ohms between the conductive wire 225 and the outer diameter of the strip 220. In alternative embodiments, a different resistance value may be used. In other alternative embodiments, the structural hoop 230 may not be used, and the continuous dock can be formed by only the strip 220 of conductive plastic and the conductive wire 225.

The strip 220 can have a diameter of 2.85 millimeters (mm) in one embodiment, although other sizes may be used in alternative embodiments. In an illustrative embodiment, the strip 220 is formed from a carbon-infused conductive plastic (PLA) that has a conductivity of 15 ohm-cm. In alternative embodiments, a different type of conductive plastic and/or a different conductivity may be used. The conductive wire 225 can be made of copper or any other highly conductive material known in the art, such as aluminum, steel, etc. As discussed in more detail below, a current is passed through the resistance of the conductive plastic of the strip 220, which warms the strip 220 and melts it, letting two such strips meld together. In addition to providing robust, orientation independent connections, this configuration also eliminates the need for a separate heating element on the robot.

In an illustrative embodiment, the conductive wire 225 is a 20-gage copper wire embedded within the strip 220 of conductive plastic that allows a uniform voltage to be applied across the entire strip 220. When two such strips having different applied voltages (e.g., one strip energized to +24V and the other strip at ground) are in contact with one another, electrical current travels primarily along the negligible resistance of the conductive wire 225 until it reaches the area closest to the contact point between the two rims. The current then travels through the conductive plastic of both strips to reach the other copper wire. This approach melts the conductive plastic in the contact region with minimal heating of the surrounding material, thus minimizing energy usage. Returning both voltages to GND stops current flow, allowing the conductive plastic to cool, rigidly attaching the two strips of conductive plastic. Reapplying the voltage again melts the plastic, weakening the connection, and allowing the two docks to separate. Since the rim (and the conductive wire within the rim) is present along the entire length of the dock platform, attachment between two docks can occur at any location where contact occurs, regardless of the positioning, or relative orientations of the two docks. This process is described in more detail with reference to FIG. 3.

Figure 2C:
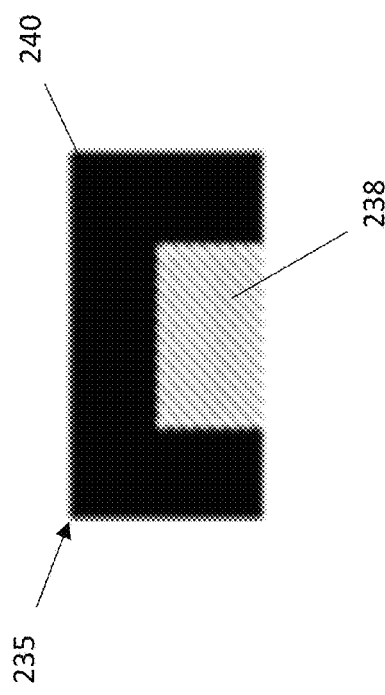
FIG. 2C is a cross-sectional view of a continuous dock that includes a highly conductive material surrounded on three sides by a moderately-conductive meltable material in accordance with an illustrative embodiment.
Figure 2D:
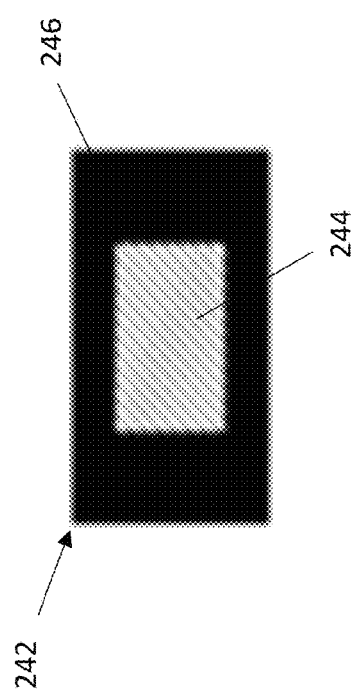
FIG. 2D is a cross-sectional view of a continuous dock that includes a highly conductive material completely surrounded by a moderately-conductive meltable material in accordance with an illustrative embodiment.
Figure 2E:
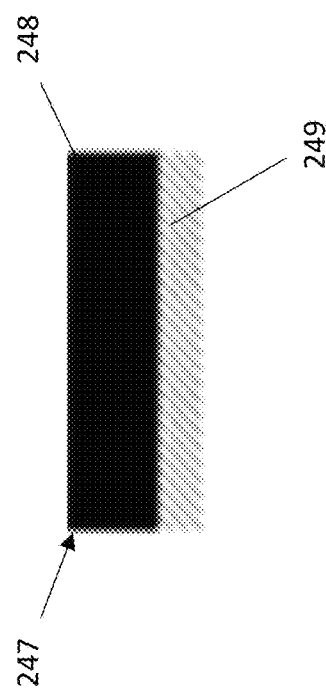
FIG. 2E is a cross-sectional view of a continuous dock that includes a moderately-conductive meltable material positioned on top of a highly conductive material in accordance with an illustrative embodiment.

FIGS. 2C-2E depict alternative configurations of the strip used to form the continuous dock. Specifically, FIG. 2C is a cross-sectional view of a strip 235 for a continuous dock that includes a highly conductive material 238 surrounded on three sides by a moderately-conductive meltable material 240 in accordance with an illustrative embodiment. FIG. 2D is a cross-sectional view of a strip 242 for a continuous dock that includes a highly conductive material 244 completely surrounded by a moderately-conductive meltable material 246 in accordance with an illustrative embodiment. FIG. 2E is a cross-sectional view of a strip 247 for a continuous dock that includes a moderately-conductive meltable material 248 positioned on top of a highly conductive material 249 in accordance with an illustrative embodiment. In alternative embodiments, different configurations may be used for the strip, and the moderately-conductive meltable material and/or the highly conductive material may have a different shape.

During attachment, it is desirable for the robot to ensure an adequate connection because locomotion can induce stresses sufficient to fracture an unsatisfactory docking connection. A connection should therefore have enough interface area to mitigate this stress (stress decreases as area increases), while achieving a temperature sufficient to melt and affix the two docks. Direct and precise measurement of the interface area and temperature of a connection typically involves a complicated array of sensors. To avoid this complexity, in one embodiment the proposed robots use a single hall-effect current sensor per dock to estimate the quality of a connection attempt based on the following principles: i) as interface area increases, resistance between docks decreases, thus increasing current, and ii) dissipated energy raises dock temperature and is proportional to the time-integral of the current. For example, a current of 0.8 amps (A) and an integrated current of 5.35 amp-seconds yields a strong connection. If 24 Volts (V) is used to form the connection, this results in an energy transfer of 130 Joules (J), which is approximately 1% of the energy in a 1000 milliAmp-hour (mAh) one cell lithium polymer battery. After achieving attachment, the dock cools for a period of time to solidify the plastic into a strong bond. In one embodiment, a conservative duration of 2 minutes cooling ensures thorough cooling of the connection. In alternative embodiments, a different cooling period of time may be used such as 30 seconds, 1 minute, 3 minutes, etc. Additionally, as discussed below, a first cooling period may be used while a motor of the robot applies pressure to the point of contact between robots and a second cooling period can be used after the pressure from the motor is removed. In an alternative embodiment, a fan can be incorporated into the robot and used to force air over the point of contact to facilitate more rapid cooling.

Figure 2F:
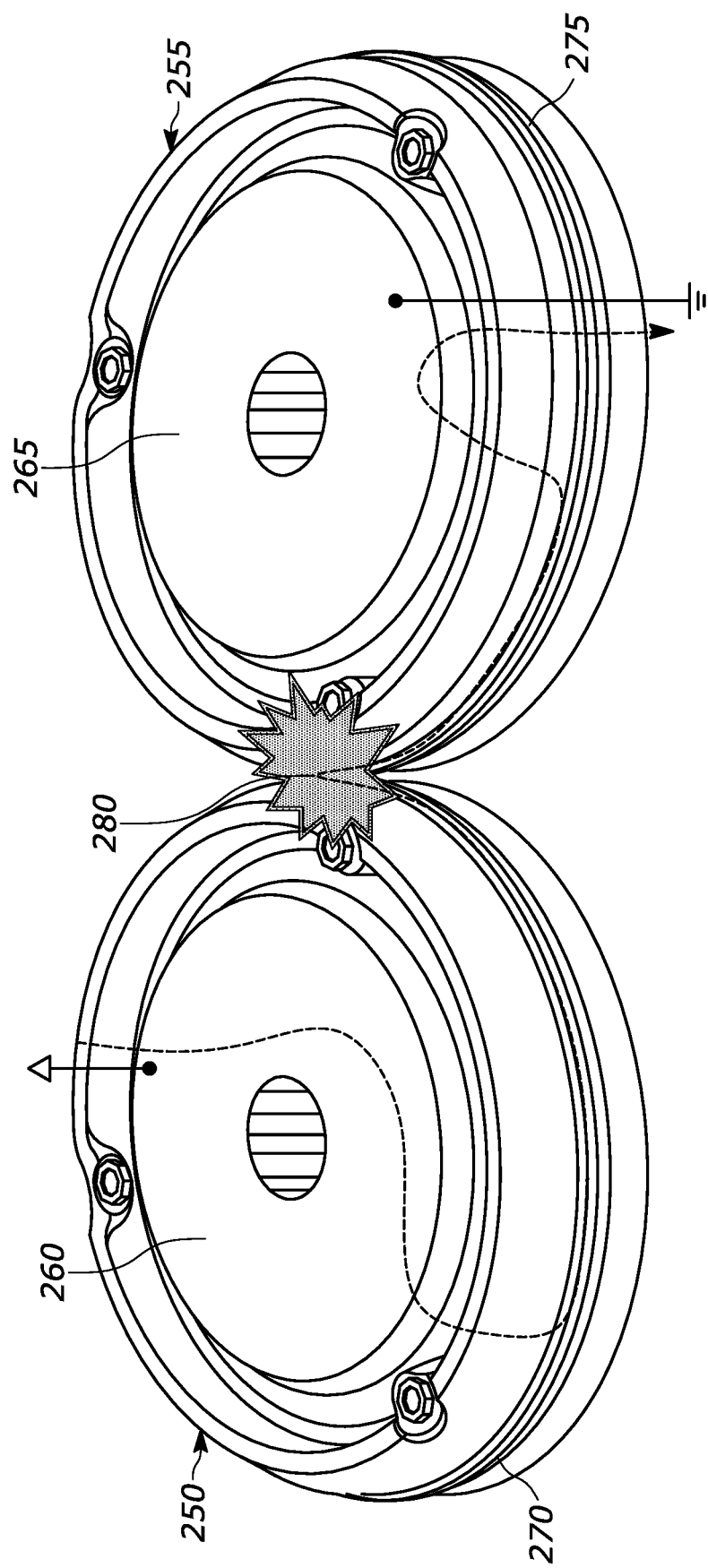
FIG. 2F depicts the flow of electricity between a first continuous dock of a first robot and a second continuous dock of a second robot in accordance with an illustrative embodiment.

FIG. 2F depicts the flow of electricity between a first continuous dock platform 250 of a first robot and a second continuous dock platform 255 of a second robot in accordance with an illustrative embodiment. The first continuous dock platform 250 includes a first wheel 260 that receives a voltage of +24V. In alternative embodiments, a different voltage may be used. A second wheel 265 of the second continuous dock platform 255 is connected to ground. A first continuous dock 270 of the first continuous dock platform 250 and a second continuous dock 275 of the second continuous dock platform 255 touch at a point of contact 280. Upon making contact, current begins to flow from the first continuous dock platform 250 to the second continuous dock platform 255. Specifically, current flows from the first wheel 260 to the conductive wire embedded in the first continuous dock 270, to the point of contact 280, to the conductive wire embedded in the second continuous dock 275, and to the second wheel 265 which is connected to ground. The current flowing through the point of contact 280 traverses the conductive plastic of the first continuous dock 270 and the conductive plastic of the second continuous dock 275, causing them to heat up and melt to one another. A cooling period is then begun such that the melted plastic hardens and forms a strong bond between the two robots.

In an illustrative embodiment, the current flow described with reference to FIG. 2F can also be used to undock (or detach) the robots from one another. To undock the robots, the 24V DC voltage is applied to the first wheel 260. The applied voltage again causes a current to flow from the first wheel 260 to the conductive wire in the first continuous dock 270, to the point of contact 280, to the conductive wire in the second continuous dock 275, and to the second wheel 265. This current causes the conductive plastic of the first continuous dock 270 and the conductive plastic of the second continuous dock 275 to melt such that the robots can readily detach from one another.

FIG. 3 depicts a power bus assembly 300 for a robot in accordance with an illustrative embodiment. The power bus assembly 300 includes a pair of top rails 305, a pair of bottom rails 310, wiring 315, and electronics 320 which allow the power bus assembly 300 to function. In an illustrative embodiment, the pair atop rails 305 is an electrically-connected pair of circular, flexible, spring-steel rails covered in a conductive material such as copper tape. Similarly, the pair of bottom rails 310 are a pair of electrically-connected circular, flexible, spring-steel rails covered with a conductive material. Alternatively, a different type of rail material and/or conductive coating material may be used. The pairs of rails are large enough to contact counterpart rails from another robot before the continuous docks of the robots make contact. Additionally, the rails are sufficiently flexible to not push away other robots. As a result, the power bus assembly rails of a first robot (powered) can contact the power bus assembly rails of a second robot (not powered) to provide power to the second robot. Specifically, current applied to the power bus assembly rails of the first robot travels through the rails of the first robot, to the point of the contact between the rails of the first and second robots, and through the rails of the second robot where it is converted into energy that powers the second robot. The power bus assembly rails are also flexible enough to allow the continuous docks of both robots to make contact once the second robot is powered.

In another illustrative embodiment, the pair of top rails 305 receive a voltage and the pair of bottom rails 310 are tied to ground. Alternatively, the pair of bottom rails 310 can receive the voltage and the pair of top rails 305 can be grounded. The voltage received by the pair of top rails 305 can be +24 V direct current (DC) in one embodiment, although a different value may be used in alternative embodiments. In another alternative embodiment, the pair of bottom rails 310 may also receive a voltage that differs from that applied to the pair of top rails 305. The wiring 315 is used to transfer the 24V DC power to the main body of the robot to provide power to the continuous docks and to the electronics and motors.

In an illustrative embodiment, the robots described herein do not use batteries due to concerns about power draw from the motors and continuous docks. Instead, the robot receives electricity through the power bus assembly 300, allowing a plurality of robots to receive power from one powered robot. Similar to the full-body continuous docks, the power bus assembly 300 allows power transfer regardless of contact location or orientation between robots, which results in the design depicted in FIG. 3.

Other benefits of using a power bus assembly in place of a battery include reduced weight and cost. A configuration able to deliver 24V to the continuous docks would weigh 650 g (increasing robot weight by ~40%) and would also increase the robot cost. Increasing weight is of particular concern since it would increase forces induced during locomotion, and any self-assembled structures would bear a greater weight. The power bus assembly configuration also ends the need to recharge robots between uses, and offers an uncomplicated way to activate robots since the robots power on as soon as they receive electricity from the power bus assembly.

Figure 4:
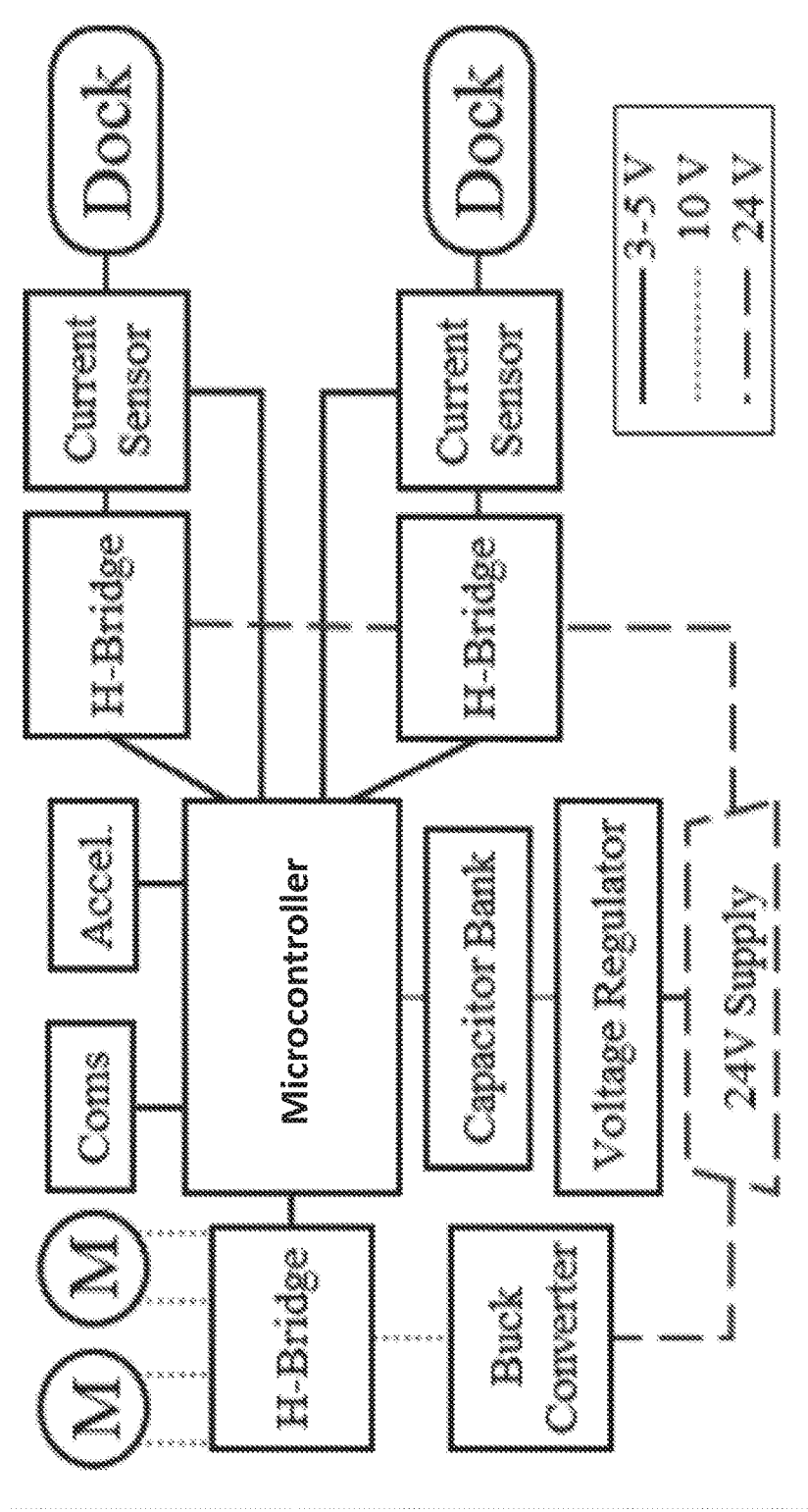
FIG. 4 is a block diagram for an electronics and motors unit of a robot in accordance with an illustrative embodiment.

FIG. 4 is a block diagram for an electronics and motors unit of a robot in accordance with an illustrative embodiment. In an illustrative embodiment, the electronics and motors unit includes a microcontroller as the platform for the electronics of the robot. In one embodiment, an Arduino Uno can be used as the microcontroller because it allows for straightforward hardware and software development. Alternatively, any other type of processor(s) and/or controller(s) may be used. In an illustrative embodiment, the electronics and motors unit receives power from the 24V supply of the power bus assembly. The continuous docks use this voltage directly, while a regulator and a buck converter bring the voltage to a usable level for the microcontroller and the motors (M), respectively. A capacitor bank stores power and helps to ensure that the microcontroller does not restart if the power bus momentarily loses connection. As indicated in the legend of FIG. 4, solid lines between components represent a voltage of 3-5V, dotted lines between components represent a voltage of 10V, and dashed lines between components depict a voltage of 24V. In alternative embodiments, different voltages may be used.

The motors, which are attached to the continuous docks, allow the robot to move by flipping about an attached dock, as depicted and described with reference to FIG. 5. An accelerometer allows the robot to measure its rotational speed and to control motor speed with a closed-loop proportional controller. This prevents the robot from flipping too quickly and slamming into the attachment surface (potentially breaking an attachment). The motors also press docks together during attachment with a force of 1.2 kg (which is ~110% of the robot's weight), and pull docks apart during disconnection. An H-bridge is used to control power provided to the motors.

The electronics and motors unit uses H-bridges to control each of the two continuous docks, tying them to GND, +24V, or a high-Z state. In an alternative embodiment, one or more power MOSFETS may be used in place of the H-bridges. Hall-effect current sensors measure current flow through the two docks. This allows the robot to track attachment progress, and to detect when a dock at +24V contacts a dock at GND (i.e., current begins to flow upon contact). Time sensors also allow closed-loop control of dock current via pulse width modulation (PWM) control of the H-bridges.

As discussed above, the H-bridges can be used to place the docks into one of three states, namely a ground (GND) state, a +24V state, or a high-Z state. In an illustrative embodiment, these three H-bridge states correspond to different dock behaviors. For example, a robot seeking connections can connect its dock to +24V, and a robot accepting connections can connect its dock to GND. Upon contact between two such robots, current flows between the two docks, allowing attachment to begin. If a robot does not wish to accept attachments (as may occur in swarm algorithms), the robot can force a dock into a high-Z state, preventing current flow between itself and a contacting dock, and thereby blocking any connections or disconnections.

The robot can also use its docks as a means of local communication between robots, as represented by the Coms block of FIG. 4. Simple messages such as "I'm seeking a connection" (+24V), or "I'm accepting connections" (GND) are inherent in the voltage of the dock, and are received by a robot either through monitoring current flow (if at +24V or GND), or by monitoring the output of a comparator circuit (if in high-Z). Additionally, since the robot can rapidly change the voltage level of its dock, more complex messages can also be exchanged. For example, one dock of a first robot can send a low duty-cycle, 24V, 100 kHz PWM signal to a touching (but not attached) dock of a second robot. A microcontroller can be used to monitor the output of a comparator connected to the receiving dock, and can interpret the signal. Other variations of signals can also be used such as different voltages, high duty vs. low duty, different frequencies, etc. The robots can be programmed to associate certain messages/instructions with each of the variations. In one embodiment, low power electrical pulses can be transmitted across a docking connection to facilitate communication without heating the connection. The Coms block also encompasses other communication systems present on the robot, either local, global, or some combination thereof. Additional examples of possible communication systems can be systems such as a Wi-Fi system, a Bluetooth® system, a bespoke system such as an infrared communication system, a vibration-based messaging system, etc.

Figure 5C:
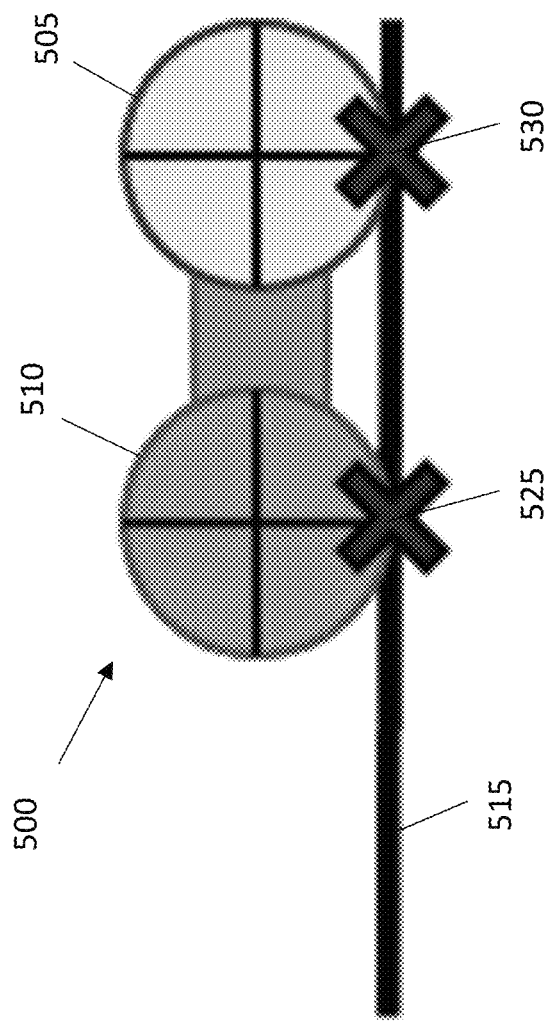
FIG. 5C depicts the robot with the first continuous dock docked at a new location on the surface in accordance with an illustrative embodiment.

FIGS. 5A-5C depict movement of a robot 500 in accordance with an illustrative embodiment. Specifically, FIG. 5A depicts the robot 500 with both of its continuous docks 505, 510 docked to a surface 515 in accordance with an illustrative embodiment. FIG. 5B depicts the robot 500 with the first continuous dock 505 detached from the surface such that the robot 500 is able to flip over in accordance with an illustrative embodiment. FIG. 5C depicts the robot 500 with the first continuous dock 505 docked at a new location on the surface 515 in accordance with an illustrative embodiment. As shown, the robot 500 moves via a flipping motion in this embodiment.

In FIG. 5A, the first continuous dock 505 of the robot 500 is docked to the surface 515 at a first point of contact 520 and the second continuous dock 510 of the robot 500 is docked to the surface 515 at a second point of contact 525. In one embodiment, the surface can be formed from a textured, highly conductive material such as copper such that the conductive plastic is able to adhere to the surface 515. In an alternative embodiment, the surface may be formed in part from conductive plastic. A voltage differential is applied between the first continuous dock 505 and the surface 515, which causes current to flow between the first continuous dock 505 and the surface 515 at the first point of contact 520. The current causes the conductive plastic of the first continuous dock 505 to heat up at the first point of contact 520 such that the bond between the first continuous dock 505 and the surface 515 can be broken. The voltage differential can be implemented by tying the surface 515 to ground and applying a positive voltage to the first continuous dock 505, or vice versa.

Once the bond at the first point of contact 520 is sufficiently heated, the microprocessor of the robot 500 activates one or more motors to flip the first continuous dock 505 over the second continuous dock 510 (which remains docked to the surface 515 and stationary), as shown in FIG. 5B. In one embodiment, the motor associated with the (stationary) second continuous dock 510 is activated to perform the flipping motion of the first continuous dock 505. After flipping, the first continuous dock 505 is in contact with the surface 515 at a third point of contact 530. A voltage differential is again applied between the first continuous dock 505 and the surface 515, which causes current to flow between the first continuous dock 505 and the surface 515 at the third point of contact 530. The current causes the conductive plastic of the first continuous dock 505 to heat up at the third point of contact 530 such that a bond between the first continuous dock 505 and the surface 515 is formed at the third point of contact 530. A cooling period can then be used to ensure that the bond adequately hardens prior to any other movement actions by the robot 500. The movement depicted in FIGS. 5A-5C can be repeated until the robot 500 is in a desired location.

A number of tests were performed to assess the strength of the bonds formed by the robots described herein. In one test, two continuous docks were pressed together with a nominal force of 750 g. This mimics a scenario in which a robot is upside down and must push against gravity, which is a worst-case scenario. The two continuous docks were melted together and cooled by a test rig using the same integrated current and cooling time parameters as the robot. The test rig then pulled the docks in opposite directions with a tensile force of 5 kg (about the weight of five robots), and verified that the docks can sustain this load for 60 seconds. After returning the docks to a zero-tension state, the test rig melted the connection and separated them. This process was repeated across 100 trials, with the test rig spinning the continuous docks between trials to randomize the attachment location, as occurs in real-world robot locomotion. Across each of these trials, the attachment never failed, showing the real-world consistency of the continuous docks. A second test was identical to the first test, with the exception that the test rig did not spin the docks between trials, thereby causing the docks to repeatedly attach at the same location. Again, the attachment did not fail across 100 trials.

A third test was used to characterize the failure load of the continuous docks. To perform this test, the two continuous docks were attached to one another using the test rig (i.e., in the same way as the first two tests) and then hung them from a scale. This allowed manual application of a load sufficient to break the connection between the two continuous docks. Across five trials, failure occurred between 17.3 kg and 28.8 kg, with an average failure load of 23.9 kg, which is more than 20 times the weight of the robot. The test demonstrates that the continuous docks are strong enough to reliably support the weight of at least five robots.

During experimentation, three potential failure modes of a continuous dock were identified: spike formation, smoke, and tear-off. Spikes can potentially grow from the surface of the conductive plastic when a robot prematurely pulls a warm dock away from its attachment surface, causing strands of plastic to pull away and harden. The resulting spikes can increase (e.g., double) the height of the surface, making it difficult for the robot to achieve a good connection at this location in the future. Additionally, a large spike can jam the wheel of the continuous dock, making further locomotion difficult or impossible. The robot therefore employs two techniques to avoid spike formation. First, the robot passes 9.5 amp-seconds through the dock (~180% of that used for the attachment process) before pulling it away to ensure that the detaching dock is very hot, which eliminates most/all of the spikes and causes any spikes that do form to become thinner and thus weaker as temperature increases. Second, the robot is configured to spin (i.e., rotate j its continuous dock during detachment, which has the effect of collapsing any spikes that form, making future attachments easier and minimizing the risk of jamming the wheel.

The conductive plastic will emit smoke when the temperature of the plastic reaches its smoking point. An attachment occurring under such conditions is often strong enough to use, but can sometimes be very weak. In extreme instances, the conductive plastic carburizes, limiting the strength of future attachments. A smoke failure can occur when a segment of the conductive plastic is barely offset from the attachment surface, causing electricity to arc across the gap. To prevent this arcing, the robot uses one or more of its motors to press the continuous dock firmly against the attachment surface to close any small gaps. Another cause of smoke is by allowing too much current to pass through the dock. To prevent this, an integrated current limit is used. Because a smoke failure can be catastrophic, the integrated current limit is the criterion used by the robot to decide when to turn off a dock and complete the attachment. Using a minimum-current threshold as the criterion for a completed bond (current is a proxy for contact area) is untenable since there is no guarantee that the desired current will occur prior to a smoke failure. Fortunately, the high strength of the dock allows the robot to function even if it does not achieve the ideal minimum current of 0.8 A.

Tear-off failures are sudden, and tend to occur when the robot presses its forward continuous dock into the attachment surface, inducing a bending moment at the rear continuous dock and allowing the rear motor to tear the dock from its attachment. Most such failures result in a clean break and do not affect the ability of the dock to form new connections. Tear-off most often occurs when the prior attachment used a spiked part of the dock, or when a small smoke-event occurred, highlighting the importance of the previously-described mitigation behaviors. Another cause of tear-off can be the robot flipping too quickly and slamming into the attachment surface, which induces a large dynamic load. The robot counteracts this by using a slow flip speed of 5.25 rotations per minute (rpm), which can be controlled using the accelerometer. In alternative embodiments, a different flip speed may be used such as 3 rpm, 4, rpm, 5 rpm, 6 rpm, etc.

Figure 6:
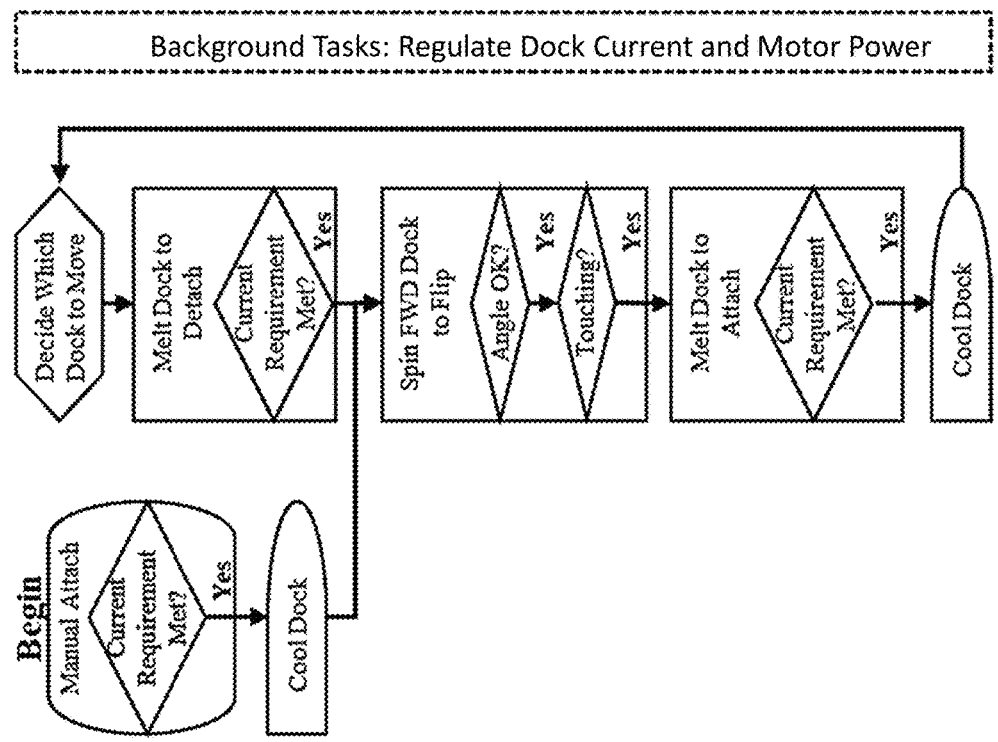
FIG. 6 is a finite state machine depicting operations to dock and un-dock a robot in accordance with an illustrative embodiment.

One design goal of the robot is to use the continuous docks to climb over copies of itself, which is a critical ability for modular robots and self-assembling structures. As a demonstration of this capability, an arena including three inert copies of the robot was constructed. The arena was tilted to an angle of 50° from horizontal. To traverse the arena, the robot executed the finite state machine shown in FIG. 6 to perform the flipping locomotion shown in FIG. 5. During execution of this finite state machine, the robot controls the dock current down to 0.8 A, and controls the motor speed to allow for a soft contact when flipping. For the first attachment only, one dock of the robot was held to let it push itself into the attachment surface. Upon satisfaction of the current requirement (e.g., time-integral of current equal to 5.35 amp-seconds), the initial connection is cooled and the finite state machine enters the third operation of its main loop and the robot begins to flip.

Referring now to the main loop of the state machine, in the first operation the robot decides which dock it will move. For purposes of the test performed, the robot simply alternates between the two continuous docks. The moving continuous dock then energizes itself and begins melting its connection so that it will be free to move. After the time-integral of the current reaches its threshold (e.g., 9.5 amp-seconds), the motor attached to the stationary dock begins to rotate, lifting the now-molten surface of the moving dock away from its prior attachment. The moving dock also spins to mitigate spike formation. Once the robot flips ~30° from its starting orientation (guaranteeing it has disconnected), the moving dock stops spinning and the robot starts checking the current sensor of the moving dock. In alternative embodiments, the angular threshold for determining when to stop spinning of the moving dock can be different from 30°, such as 32°, 35°, etc. If current flows from the still-energized dock, the robot knows that the moving dock has contacted a robot (or other surface) that accepts attachments. In one embodiment, the robot uses a touching-current threshold of 0.4 A to ensure it has found a good attachment location. In alternative embodiments, a higher or lower touching-current threshold may be used. If the robot does not find a good attachment location in 30 seconds, it stops pressing the moving dock against the surface and briefly spins the moving dock to expose a different part of the conductive plastic. This attachment-seeking behavior repeats until a good attachment location is identified.

After finding a good contact location, the robot presses the moving dock into the attachment surface with the full power of its motor (about 1.2 kg of force). In alternative embodiments, a motor of different strength and/or a different pressing force may be used. The moving dock then melts into the attachment surface until the time-integral of the current reaches the attachment threshold (e.g., 5.35 amp-seconds), after which the moving dock de-energizes. The newly-formed attachment cools for a first cooling period of 80 seconds while the motor of the robot continues to press the moving dock into the attachment surface. A second cooling period of 40 seconds then occurs with all motors turned off, allowing the motor H-bridge and motors to cool. In alternative embodiments, different values for the first and/or second cooling periods may be used. The main loop of the finite state machine then repeats. During implementation of the main loop, the microcontroller regulates the dock current and motor power to achieve the desired movement, force values, and time-integral of current values set forth herein.

Using the processes of the state machine described above, the robot was able to complete a lap around the arena in 11 flips over a duration of 28 minutes. Of the 28 minute duration, the robot spent 80% of the time cooling after attachment. Although a shorter cooling duration would hasten locomotion, a conservative duration helps ensure a good attachment. In traversing the arena, the robot demonstrates its ability to move over copies of itself at any orientation (including upside-down) without the need for alignment mechanisms or complicated sensing.

FIGS. 7A-7D depict illustrative usage variants of the of the technology described herein, which is not limited to robotic attachment. As discussed above, the systems and methods described herein can also be used in place of fasteners, to mount accessories onto a dock, to mount artwork, in place of an adhesive, etc. The systems and methods can also allow robots to pick up items and mount themselves and/or the items to various surfaces. In FIGS. 7A-7D, the solid lines depict electrical wiring and the dashed lines depict current flow. Also, a GND can be used in place of either V+ or V−. Each of the docks in FIGS. 7A-7D includes a highly conductive material 700 and a moderately-conductive meltable material 705 (e.g., conductive plastic) as described herein.

Figure 7A:
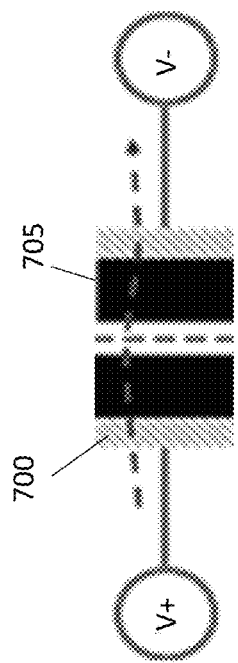
FIG. 7A depicts current flow between homogeneous docks in accordance with an illustrative embodiment.
Figure 7B:
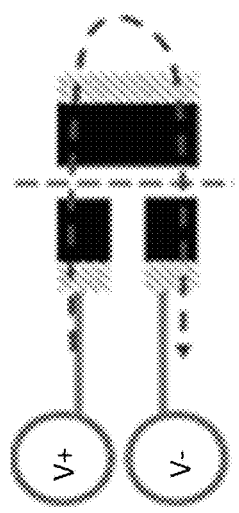
FIG. 7B depicts current flow between a heterogeneous dock and a homogeneous dock in accordance with an illustrative embodiment.
Figure 7C:
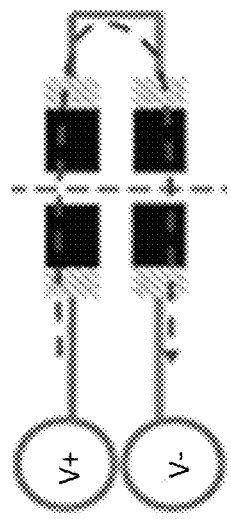
FIG. 7C depicts current flow between heterogeneous docks using switchable electronics in accordance with an illustrative embodiment.
Figure 7D:
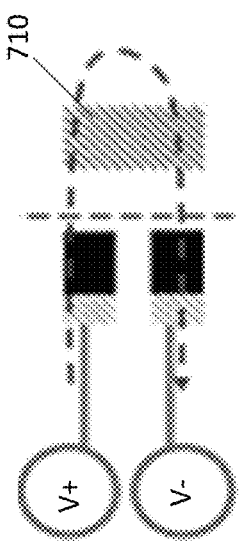
FIG. 7D depicts current flow between a dock and a surface in accordance with an illustrative embodiment.

FIG. 7A depicts current flow between homogeneous docks in accordance with an illustrative embodiment. As an example, FIG. 7A can represent the process performed to dock or un-dock identical continuous dock platforms (each having a single continuous dock) to one another. FIG. 7B depicts current flow between a heterogeneous dock and a homogeneous dock in accordance with an illustrative embodiment. For example, FIG. 7B can represent the process performed to dock or un-dock a continuous dock platform having two continuous docks (or rims) to a continuous dock platform (or other surface/object) having a single rim. FIG. 7C depicts current flow between heterogeneous docks using switchable electronics in accordance with an illustrative embodiment. As an example, FIG. 7C can represent the process performed to dock or un-dock two continuous dock platforms which each have two rims. FIG. 7D depicts current flow between a dock and a surface 710 in accordance with an illustrative embodiment. The surface can be a textured, highly conductive surface that is not necessarily the same as the highly conductive material used in the dock. The surface can be part of a platform to which a robot is attempting to dock/un-dock or part of an object that the robot is picking up. In alternative embodiments, different current flow configurations may be used. For example, a heterogeneous dock-conductor configuration may be used in one embodiment.

The continuous docks described herein are not limited to a particular form factor or to a particular type/shape of robotic platform. For example, instead of a conductive wire to carry current and melt a plastic, the continuous dock can utilize a conductive sheet or plate, a conductive mesh, etc. Additionally, instead of a wheel type continuous dock such as the continuous dock 200 depicted in FIG. 2A, the continuous dock may be linear, spherical, semi-spherical, a flat sheet of varying shape, a curved sheet, a partial wheel, etc. Also, different types of continuous docks can connect to one another using the techniques described herein. For example, a semi-spherical continuous dock can be joined to a flat sheet continuous dock, a linear continuous dock can be joined to a wheel type continuous dock, etc.

Figure 8:
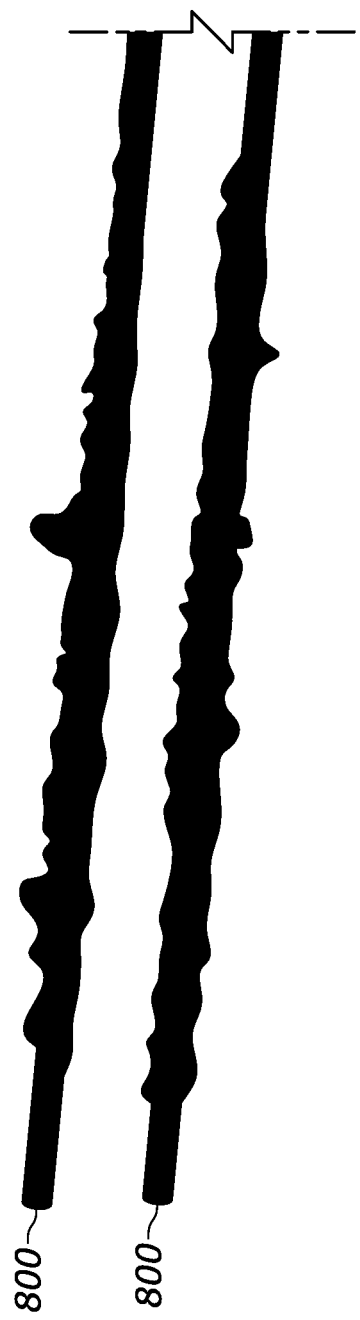
FIG. 8 depicts linear continuous docks in accordance with an illustrative embodiment.
Figure 9:
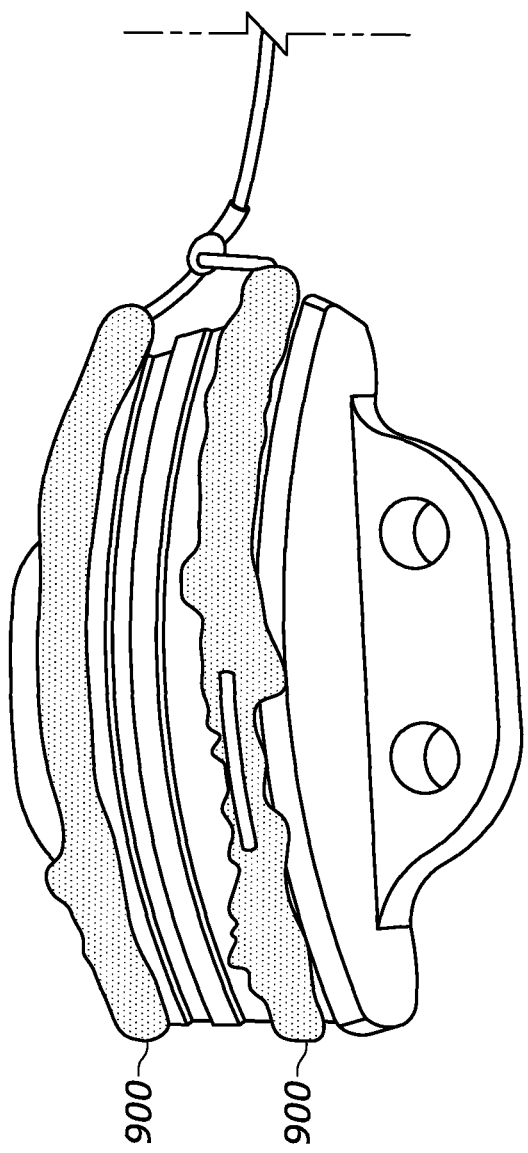
FIG. 9 depicts a partial wheel continuous dock in which the continuous docks are curved to match the profile of the partial wheel in accordance with an illustrative embodiment.

FIG. 8 depicts linear continuous docks 800 in accordance with an illustrative embodiment. The linear continuous docks 800 include a conductive wire surrounded by a plastic. Alternatively, instead of a wire, a flat rectangular conductive sheet may be used. The linear continuous docks 800 can be of any desired length, and any number of the linear continuous docks can be used to achieve a desired docking strength. In addition to straight line continuous docks, the continuous docks of FIG. 8 can be curved, L-shaped, U-shaped, T-shaped, etc. FIG. 9, for example, depicts a partial wheel continuous dock in which the continuous docks 900 are curved to match the profile of the partial wheel in accordance with an illustrative embodiment.

Figure 10B:
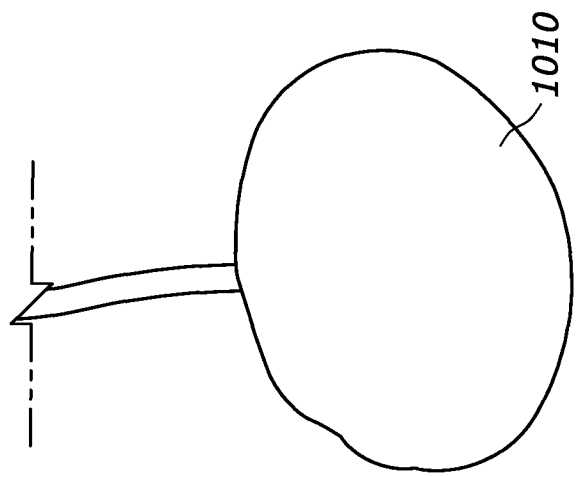
FIG. 10B depicts a circular sheet continuous dock in accordance with an illustrative embodiment.
Figure 10A:
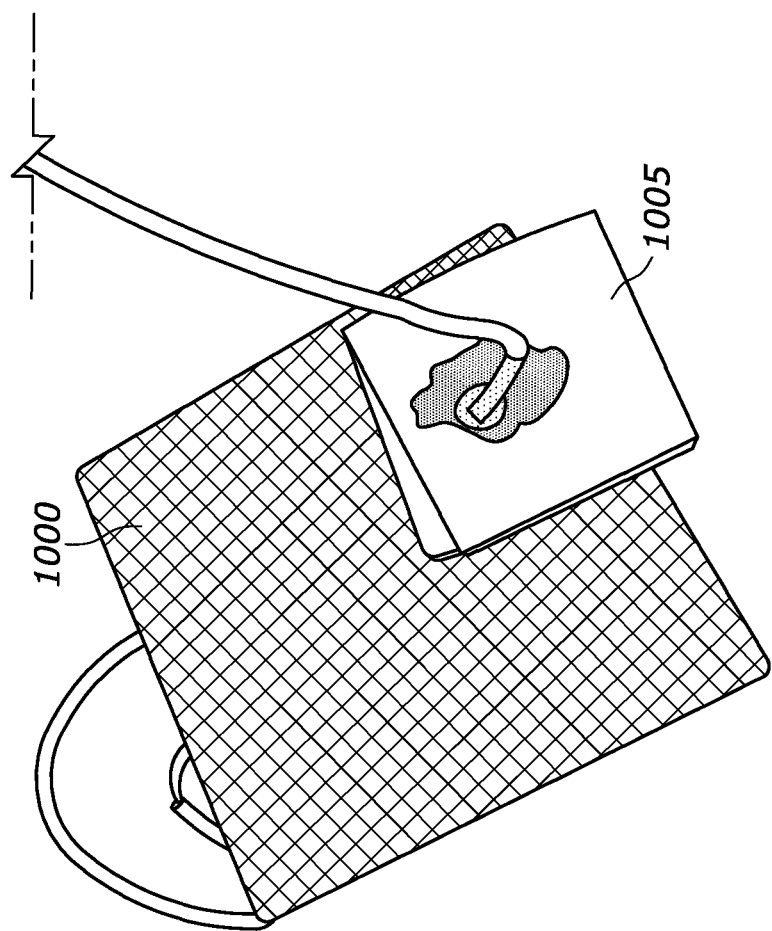
FIG. 10A depicts square sheet continuous docks mounted to one another in accordance with an illustrative embodiment.

Additional continuous dock configurations are depicted in FIGS. 10A-10H. FIG. 10A depicts square sheet continuous docks mounted to one another in an illustrative embodiment. Specifically, a first square sheet continuous dock 1000 is docked to a second square sheet continuous dock 1005. Each of the square sheet continuous docks includes a conductive sheet (e.g., copper) covered by a plastic sheet. As shown, different size docks can be docked to one another. Additionally, different shapes can be used to form sheet continuous docks such as circular, rectangular, triangular, ovular, etc. FIG. 10B depicts a circular sheet continuous dock 1010 in accordance with an illustrative embodiment. As shown, a single wire can be used to provide power/ground to the continuous dock sheets.

Figure 10C:
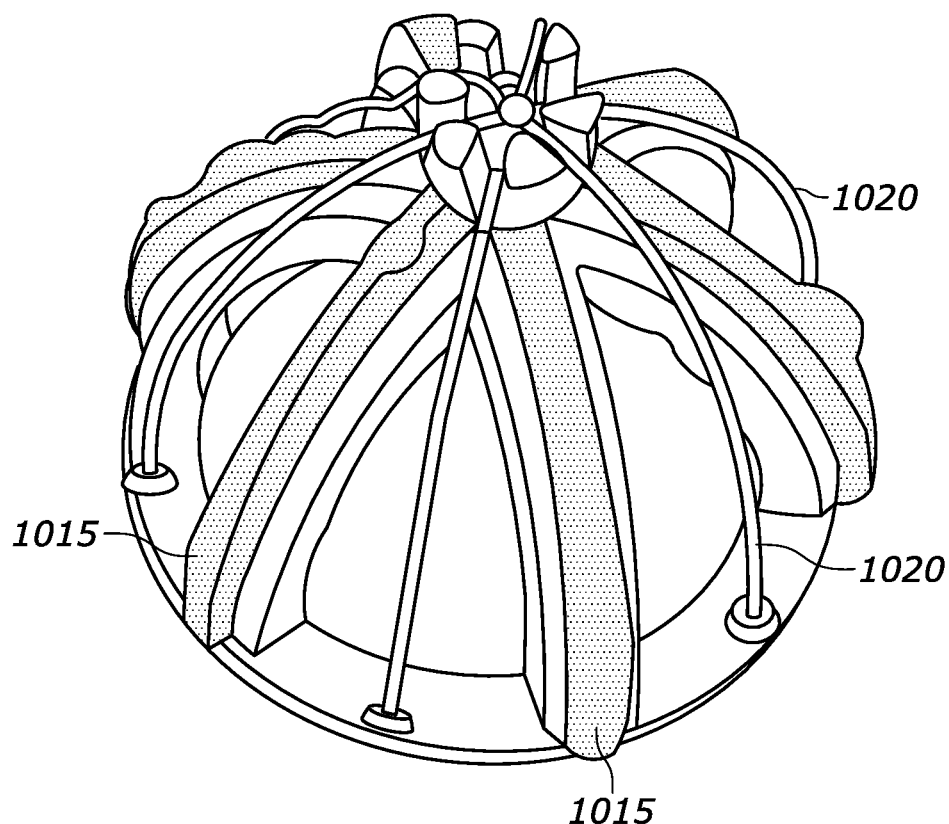
FIG. 10C depicts a semi-spherical continuous dock platform having a plurality of contoured continuous docks in accordance with an illustrative embodiment.
Figure 10D:
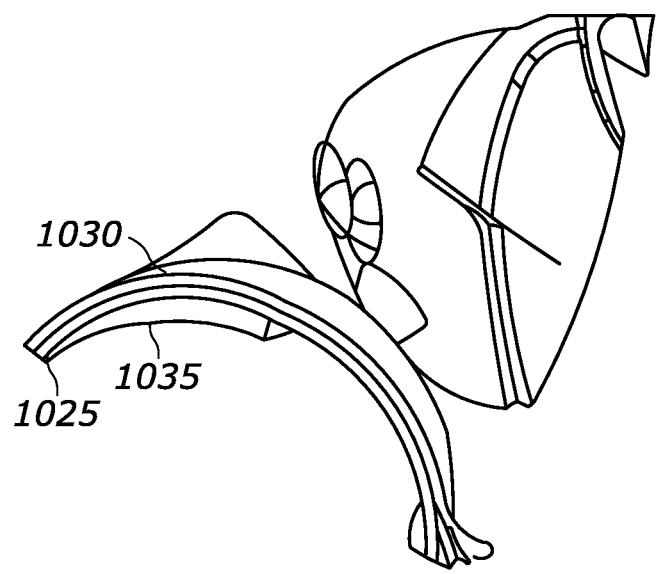
FIG. 10D depicts curved sheet continuous docks mounted to one another in accordance with an illustrative embodiment.

FIG. 10C depicts a semi-spherical continuous dock platform having a plurality of contoured continuous docks 1015 in accordance with an illustrative embodiment. The semi-spherical continuous dock platform also includes conductive wires 1020 that allow current to flow between continuous dock platforms. FIG. 10D depicts curved sheet continuous docks mounted to one another in accordance with an illustrative embodiment. Each of the curved sheet continuous docks includes a curved conductive sheet 1025 that is at least partially covered on one side by a conductive plastic 1030 and on the other side by a support plastic 1035. In one embodiment, the conductive plastic 1030 can be attached to the support plastic 1035 using fins or any other technique.

Figure 10F:
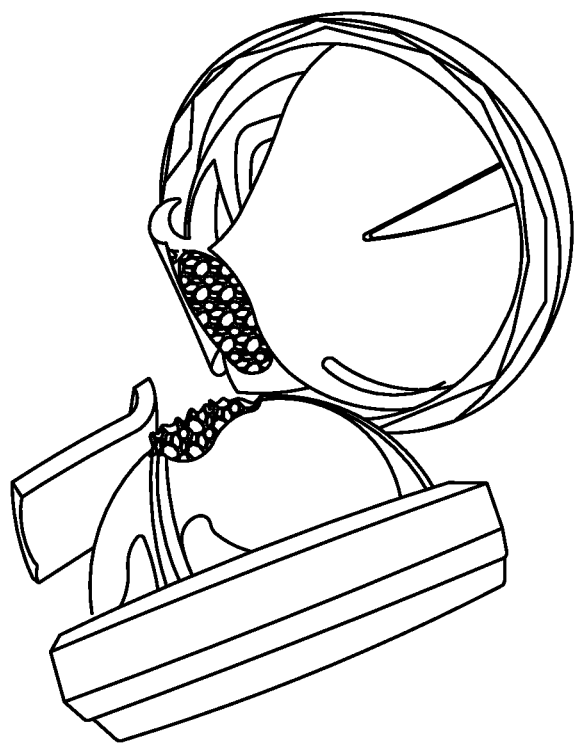
FIG. 10F depicts semi-spherical continuous dock platforms bonded to one another in accordance with an illustrative embodiment.
Figure 10E:
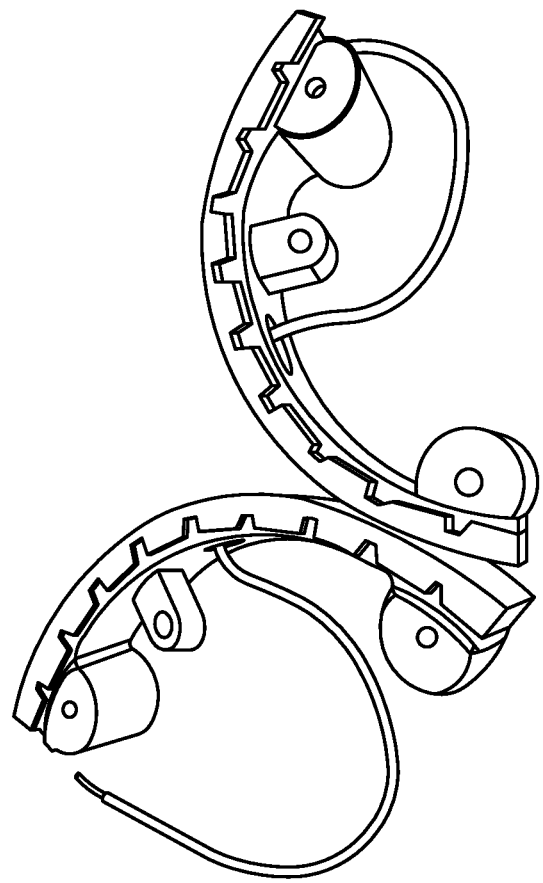
FIG. 10E depicts curved rectangular sheet continuous docks bonded to one another in accordance with an illustrative embodiment.
Figure 10H:
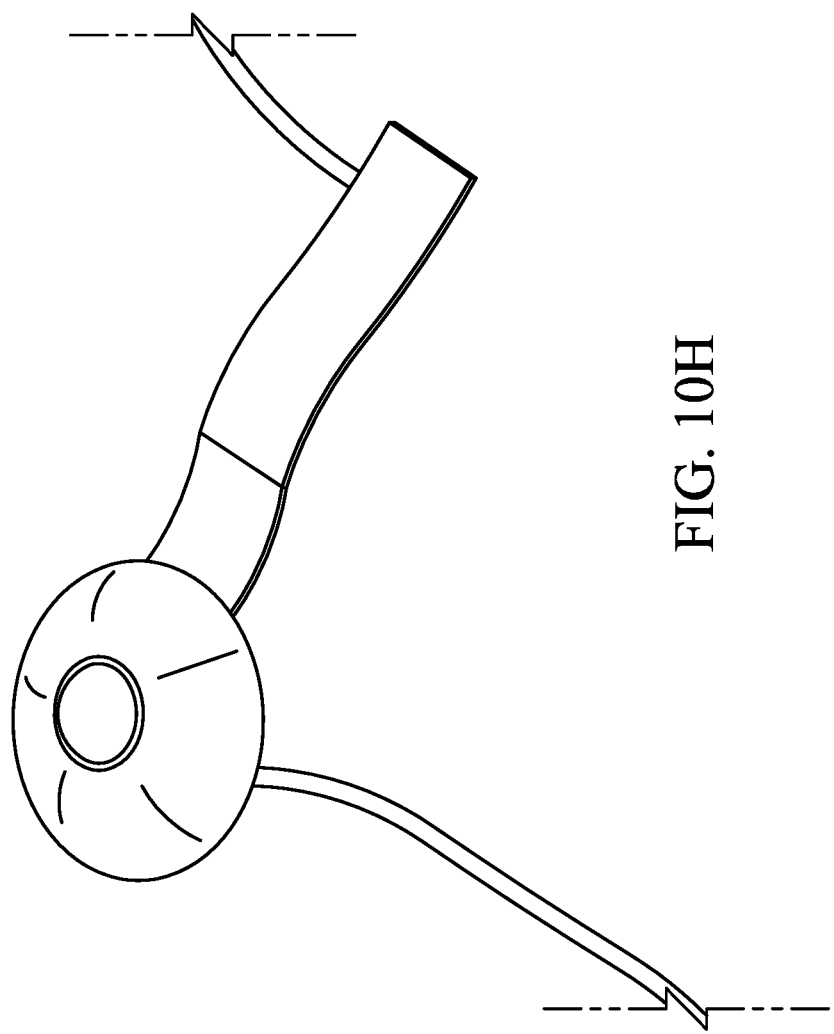
FIG. 10H depicts a curved sheet continuous dock with a central conductor in accordance with an illustrative embodiment.
Figure 10G:
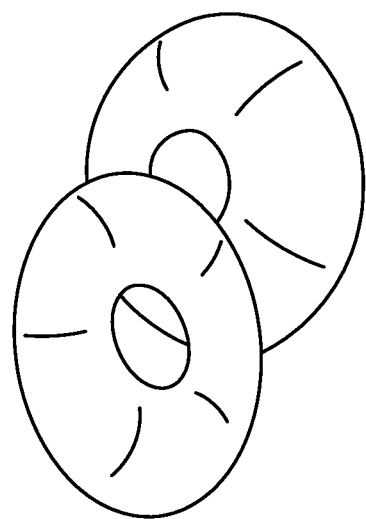
FIG. 10G depicts curved sheet continuous docks in accordance with art illustrative embodiment.

FIG. 10E depicts curved rectangular sheet continuous docks bonded to one another in accordance with an illustrative embodiment. FIG. 10F depicts semi-spherical continuous dock platforms bonded to one another in accordance with an illustrative embodiment. FIG. 10G depicts curved sheet continuous docks in accordance with an illustrative embodiment. The curved sheet continuous docks include a conductive sheet (e.g. aluminum) covered on one side with a conductive plastic. FIG. 10H depicts a curved sheet continuous dock with a central conductor in accordance with an illustrative embodiment.

Figure 11B:
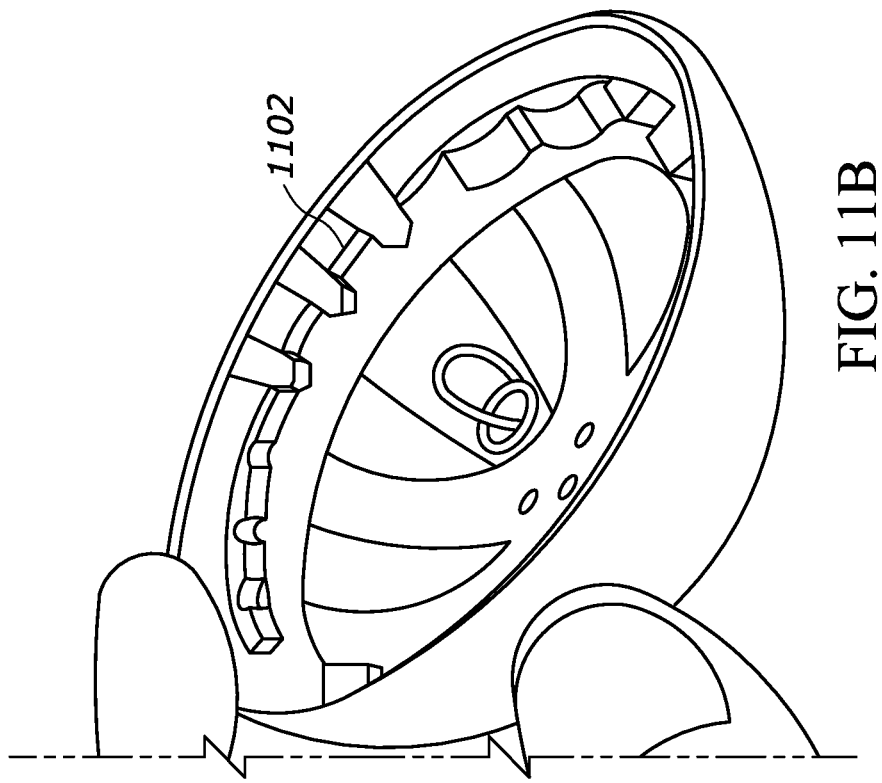
FIG. 11B depicts an inner surface of the spherical continuous dock in accordance with an illustrative embodiment.
Figure 11A:
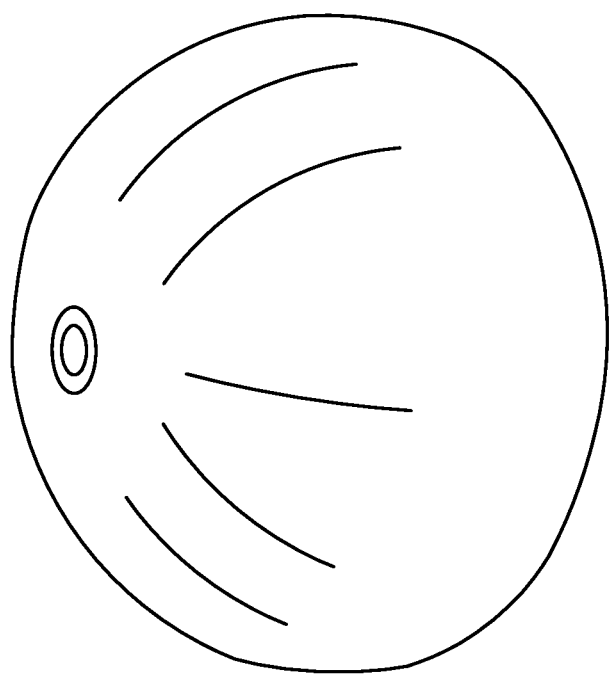
FIG. 11A depicts an outer surface of a spherical continuous dock in accordance with an illustrative embodiment.

FIG. 11A depicts an outer surface of a device that includes a spherical continuous dock in accordance with an illustrative embodiment. FIG. 11B depicts an inner surface of the spherical continuous device in accordance with an illustrative embodiment. The spherical continuous dock, which can be a full sphere or a partial sphere (e.g., semi-sphere), can be attached to a power bus, electronics, and motors similar to the other embodiments described herein. In an illustrative embodiment, the spherical continuous dock is made from a composite material that is formed in layers. As shown in FIG. 11B, the inner surface of the device includes an insulating layer 1102 that serves to insulate any systems inside of the hemisphere from the voltage on the outside of the hemisphere (i.e. the voltage applied to the continuous dock portion of the device). The insulating layer 1102 can be made from polylactic acid (PLA) or any other non-conductive material, depending on the implementation.

Figure 11D:
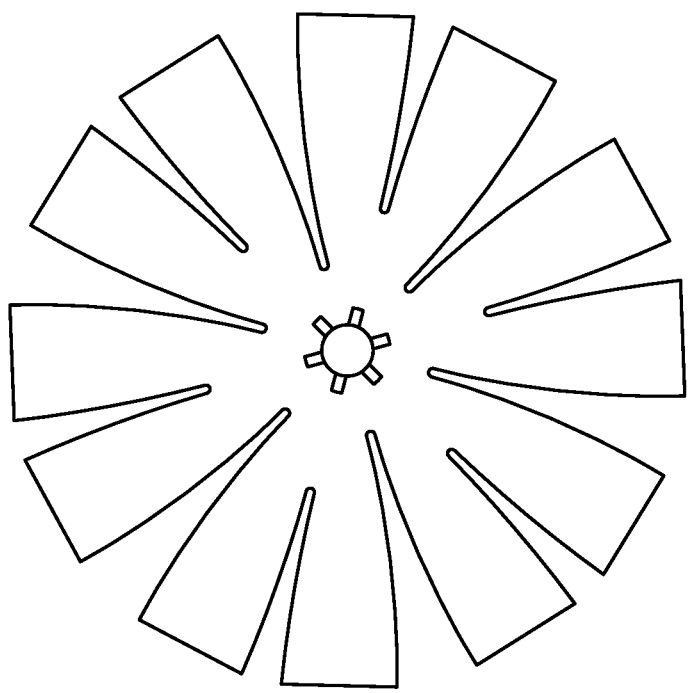
FIG. 11D depicts a 2D layer of conductive plastic in the form of a flower pattern in accordance with an illustrative embodiment.
Figure 11C:
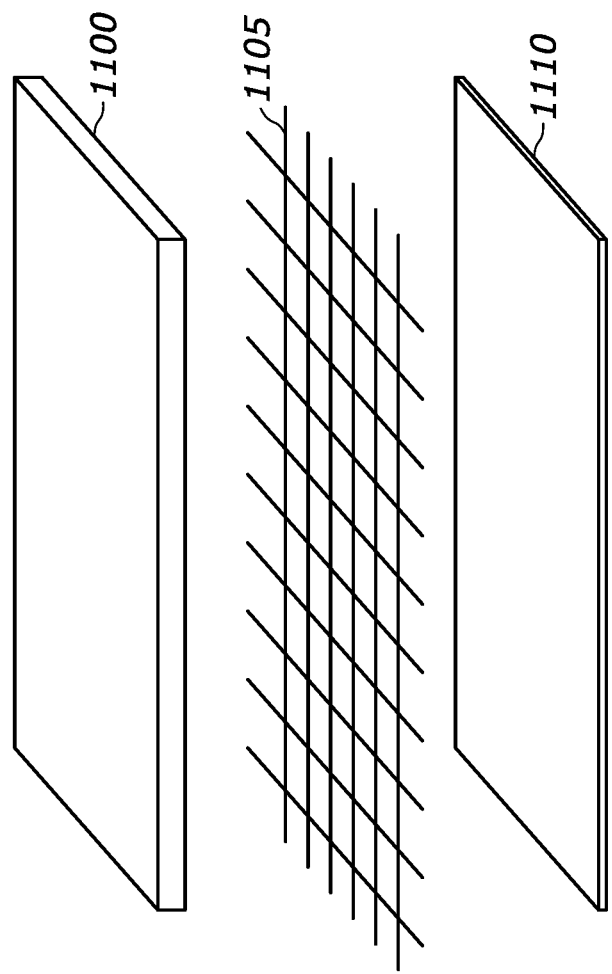
FIG. 11C is an exploded view depicting layers of the composite material used to form the continuous dock in accordance with an illustrative embodiment.

FIG. 11C is an exploded view depicting layers of the composite material used to form the continuous dock in accordance with an illustrative embodiment. As shown in FIG. 11C, the composite material that forms the spherical continuous dock includes a first conductive plastic layer 1100, a conductive weave (or conductive mesh) layer 1105, and a second conductive plastic layer 1110. In alternative embodiments, the composite material may include additional layers. In an illustrative embodiment, the first conductive plastic layer 1100 can have a first thickness (e.g., 1.4 mm) and the second conductive plastic layer 1110 can have a second thickness (e.g., 0.2 mm) that is less than the first thickness. The difference in layer thickness is driven by a difference in purpose of the two layers. The purpose of the inner layer is to bond via melting to the other (outer) layer through the holes in the mesh, thus securely encapsulating the mesh within the plastic and ensuring that the conductive plastic is the only thing touching the mesh. Thus, this inner layer does not necessarily need to be thick. The outer layer is made thicker for two main reasons. First, having a thicker outer layer allows for greater longevity since it allows for more material to be lost without consequence in an unfavorable disconnection. Second, preliminary experimentation has shown that the thickness of the material to minimize resistance was around 1.5 mm (as opposed to making the outer layer as thin as possible). In alternative embodiments, different thickness values may be used and/or the first and second conductive plastic layers can have the same thickness.

In an illustrative embodiment, the conductive weave layer 1105 is made from a copper mesh. Alternatively, a different conductive material can be used to form the conductive weave layer 1105, such as aluminum, steel, etc. To form the composite material, the conductive plastic can be printed using a three-dimensional printer, or formed using another technique such as injection molding, etc. Once formed, the layers can be pressed together with an applied heat to ensure that the layers adhere to one another and form the composite. In one implementation, two-dimensional (i.e., relatively flat) layers of the conductive plastic are formed by printing, molding, etc., and the conductive weave layer is also formed as a 2D layer. These layers are then pressed together under heat, and the 2D composite shape is formed into a hemisphere as shown in FIG. 11A. FIG. 11D depicts a 2D layer of conductive plastic in the form of a flower pattern in accordance with an illustrative embodiment. This flower pattern is readily formed into the semi-sphere shape. Alternatively, other shapes/patterns may be used to form other 3D shapes such as a cube, full sphere, etc. In another alternative embodiment, injection molding or other more efficient manufacturing techniques can be used to directly form the layers into the 3D shape.

The above-described spherical conductive layer results in strong bonding between the layers that resists delamination because the holes in the conductive weave layer (or conductive mesh) allows the conductive plastic layers to bond to one another and encapsulate the conductive mesh. Additionally, the use of a conductive mesh layer strengthens the overall composite material and prevents the conductive plastic from stretching or otherwise deforming when subjected to high temperatures.

In an illustrative embodiment, any of the systems described herein can include and/or be in communication with a computing system that includes, a memory, processor, user interface, transceiver, and any other computing components. Any of the operations described herein may be performed by the computing system. The operations can be stored as computer-readable instructions on a computer-readable medium such as the computer memory. Upon execution by the processor, the computer-readable instructions are executed as described herein.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A robot comprising:
a power bus assembly configured to receive a voltage;
a continuous dock;
a motor configured to move the robot; and
a microcontroller in communication with the motor, the power bus assembly, and the continuous dock, wherein the microcontroller is configured to:
determine that the continuous dock is in contact with a surface that results in a voltage differential between the continuous dock and the surface; and
activate the motor to apply a force that presses the continuous dock against the surface, wherein the voltage causes a current to flow from the continuous dock to the surface such that a portion of the continuous dock melts and forms a bond to the surface.

2. The robot of claim 1, further comprising a current sensor, wherein the microcontroller is configured to use the current sensor to determine that the continuous dock is in contact with the surface.

3. The robot of claim 1, wherein the continuous dock comprises a first continuous dock, and wherein the surface comprises a second continuous dock associated with a different robot.

4. The robot of claim 1, wherein the microcontroller is configured to remove the voltage from the continuous dock once an attachment threshold is met, and wherein the attachment threshold comprises a time-integral of the current.

5. The robot of claim 1, wherein the continuous dock comprises a conductive material and a conductive plastic that at least partially surrounds the conductive material.

6. The robot of claim 1, wherein the continuous dock comprises a first continuous dock having a first conductive material and a first conductive plastic, and wherein the surface comprises a second continuous dock having a second conductive material and a second conductive plastic, and wherein the current flows from the first conductive material, through a portion of the first conductive plastic, through a portion of the second conductive plastic that is in contact with the portion of the first conductive plastic, and to the second conductive material.

7. The robot of claim 6, wherein the current causes the first conductive plastic and the second conductive plastic to melt and form the bond.

8. The robot of claim 1, wherein the continuous dock comprises a first continuous dock, and further comprising a second continuous dock in communication with the power bus assembly and the microcontroller, wherein the microcontroller causes the second continuous dock to flip over the first continuous dock that is bondable to the surface to move the robot, and wherein the microcontroller applies the voltage to the second continuous dock to bond the second continuous dock to the surface.

9. The robot of claim 8, wherein the microcontroller is configured to reapply the voltage to the first continuous dock such that the current flows from conductive material in the first continuous dock, and through a portion of conductive plastic of the first continuous dock that contacts the surface such that the conductive plastic melts and weakens the bond between the first continuous dock and the surface.

10. The robot of claim 9, further comprising a current sensor, wherein the microcontroller is configured to use the current sensor to determine whether a time integral of the current satisfies a detachment threshold.

11. The robot of claim 10, wherein the detachment threshold comprises 9.5 amp-seconds.

12. The robot of claim 9, wherein the microcontroller causes the first continuous dock to flip over the second continuous dock that is bonded to the surface to break the bond between the first continuous dock and the surface and to further move the robot.

13. The robot of claim 12, wherein the microcontroller causes the first continuous dock to spin during a least a portion of the flip of the first continuous dock.

14. The robot of claim 12, further comprising an accelerometer to monitor a rate at which the first continuous dock flips over the second continuous dock.

15. The robot of claim 1, wherein the microcontroller is configured to:
remove the voltage from the continuous dock; and
cause the robot to remain stationary during a cooling period such that the bond hardens.

16. The robot of claim 15, wherein the cooling period comprises a first cooling period during which the motor continues to apply the force to press the continuous dock against the surface and a second cooling period during which the motor no longer applies the force.

* * * * *